(12) United States Patent
Fox et al.

(10) Patent No.: US 8,214,153 B1
(45) Date of Patent: Jul. 3, 2012

(54) METHODS FOR DETERMINING THE GENETIC AFFINITY OF MICROORGANISMS AND VIRUSES

(75) Inventors: George E. Fox, Houston, TX (US); Richard C. Willson, III, Houston, TX (US); Zhengdong Zhang, Houston, TX (US)

(73) Assignee: Technology Licensing Co. LLC, Palm Harbor, FL (US)

( * ) Notice: Subject to any disclaimer, the term of this patent is extended or adjusted under 35 U.S.C. 154(b) by 1785 days.

(21) Appl. No.: 10/057,270

(22) Filed: Jan. 26, 2002

Related U.S. Application Data

(60) Provisional application No. 60/264,403, filed on Jan. 26, 2001.

(51) Int. Cl.
*G01N 33/48* (2006.01)
*G01N 33/50* (2006.01)

(52) U.S. Cl. ......................................................... 702/19

(58) Field of Classification Search .................. None
See application file for complete search history.

(56) References Cited

U.S. PATENT DOCUMENTS

| | | | |
|---|---|---|---|
| 4,851,330 A | | 7/1989 | Kohne |
| 5,217,862 A | * | 6/1993 | Barns et al. ................. 435/6 |
| 5,288,611 A | | 2/1994 | Kohne |
| 5,932,220 A | * | 8/1999 | Barbour et al. ............ 424/190.1 |
| 6,738,502 B1 | * | 5/2004 | Coleman et al. ............. 382/133 |
| 6,797,817 B1 | * | 9/2004 | Ebersole et al. ............. 536/24.3 |

OTHER PUBLICATIONS

Fox, Comparative cataloguing . . . Systemics Intn, J. Syst. Bacteriol 27, 44-57 (1977).
Fox, The phylogeny of proKargotes Science 209, 454-463 (1980).
Maidak, The RDP., . continues Nucleic Acids Res. 28, 173-174(2000).
McGill et al, Characteristic . . . oligonucleotides Syst. Microbiol., 7, 194-197 (1986).
Uchida et al, The use of . . . Determination J. Molec Evol. 3, 63-77 (1974).
Woese, Bacterial evolution Microbiol. Rev., 51, 221-271 (1987).
Woese, Phylogenetic . . . mycoplasmas Proc. Natl Acad. Sci. 77, 494-498, 1980.
Woese et al, The phylogeny . . . subdivision Proc. Natl Acad. Sci. 77, 494-498 (1984).
Woese et al, A phylogenetic . . . Taxa system Appl Microbiol, 6, 143-151 (1985).

* cited by examiner

*Primary Examiner* — Jason Sims
(74) *Attorney, Agent, or Firm* — Richard Coale Willson, Jr.

(57) ABSTRACT

Selecting which sub-sequences in a database of nucleic acid such as 16S rRNA are highly characteristic of particular groupings of bacteria, microorganisms, fungi, etc. on a substantially phylogenetic tree. Also applicable to viruses comprising viral genomic RNA or DNA. A catalogue of highly characteristic sequences identified by this method is assembled to establish the genetic identity of an unknown organism. The characteristic sequences are used to design nucleic acid hybridization probes that include the characteristic sequence or its complement, or are derived from one or more characteristic sequences. A plurality of these characteristic sequences is used in hybridization to determine the phylogenetic tree position of the organism(s) in a sample. Those target organisms represented in the original sequence database and sufficient characteristic sequences can identify to the species or subspecies level. Oligonucleotide arrays of many probes are especially preferred. A hybridization signal can comprise fluorescence, chemiluminescence, or isotopic labeling, etc.; or sequences in a sample can be detected by direct means, e.g. mass spectrometry. The method's characteristic sequences can also be used to design specific PCR primers. The method uniquely identifies the phylogenetic affinity of an unknown organism without requiring prior knowledge of what is present in the sample. Even if the organism has not been previously encountered, the method still provides useful information about which phylogenetic tree bifurcation nodes encompass the organism.

21 Claims, 15 Drawing Sheets

| GUGCACC | matchingTimes | 3 | |
| | matchedOrg | E.colik12 | ∅ |
| | | B.subtilis | ∅ |
| | | Sncy.6803b | ∅ |
| | treeNodeValues | 301 | 1.00 |
| | | 305 | 0.95 |
| | | 402 | 0.83 |
| | | 465 | 0.71 |
| | | 590 | 0.64 |
| UCGGGAC | matchingTimes | 4 | |
| | matchedOrg | Acp.laidla | ∅ |
| | | Cor.xerosi | ∅ |
| | | Hel.cholra2 | ∅ |
| | | C.leptum | ∅ |
| | treeNodeValues | 2304 | 1.00 |
| | | 2305 | 1.00 |
| | | 2310 | 0.94 |
| | | 2323 | 0.76 |
| | | 2330 | 0.58 |

Figure 2

```
E.colirnA3.gb

LOCUS       E.colirnA3    3714 bp    RNA            RNA       09-NOV-1998
DEFINITION  Escherichia coli str. MG1655 [gene=rrsA gene].
REFERENCE   1
  AUTHORS   Blattner,F.R., Plunkett,G.,III, Bloch,C.A., Perna,N.T., Burland,V.,
            Riley,M., Collado-Vides,J., Glasner,J.D., Rode,C.K., Mayhew,G.F.,
            Gregor,J., Davis,N.W., Kirkpatrick,H.A., Goeden,M.A., Rose,D.J.,
            Mau,B. and Shao,Y.
  TITLE     The complete genome sequence of Escherichia coli K-12.
  JOURNAL   Science 277 (5331), 1453-1474 (1997)
COMMENT
            Corresponding GenBank entry: U00096 (bases 4033120 to 4034661)
            legacy_attribute= CG Site No. 189
            operon= rrsA gene
            isolate_name= MG1655
BASE COUNT      389 a    352 c    487 g    314 u    2172 others
ORIGIN
        1 ~~~~~~~~~~ ~~~~~~~~~~ ~~~~~~~~~~ ---AAAUUGA A-GAGUU-U- GA-U-CAU-G
        .
        .
     3541 -GUAGG-GGA -A-CCUG--C GGU--UG-GA UCACCUCCUU A--------- ----------
     3601 ---------- ---------- ---------- ------------------- ----------
     3661 ---------- ---------- ---------- ------.... ...........  ....
//
```

⇓ readseq

```
E.colirnA3.fasta

>E.colirnA3   3714 bp   RNA     RNA    09-NOV-1998, 3714 bases, 1504 checksum.
---------------------------------AAAUUGAA-GAGUU-U-
GA-U-CAU-G
.
.
GUAGG-GGA-A-CCUG--CGGU--UG-GAUCACCUCCUUA----------
--------------------------------------------------
----.................
```

⇓ fasta2flat

```
E.colirnA3.fasta.converted

E.colirnA3     AAAUUGAAGAGUUUGAUCAUG...GUAGGGGAACCUGCGGUUGGAUCACCUCCUUA
```

Figure 4

Figure 10A-10C The representative prokaryotic phylogenetic tree in Newick format.

Figure 10A

'<Msr.barker> Methanosarcina barkeri str. 227 DSM 1538' : 0.13236 , '<Msp.hungat> Methanospirillum hungatei str. JF1 DSM 864 (T)' : 0.16948 ) : 0.24421 , '<Hf.volcani> Haloferax volcanii str. DS-2 ATCC 29605 (T) : 0.03648 ) : 0.09112 , ('<env.SBAR16> Santa Barbara Channel bacterioplankton DNA clone SBAR16' : 0.19448 , '<Tpl.acidop> Thermoplasma acidophilum str. 122-1B2' : 0.22004 ) : 0.04224 ) : 0.10775 , '<Arg.fulgid> Archaeoglobus fulgidus str. VC-16 DSM 4304 (T)' : 0.04075 ) : 0.05544 , ('<Mb.formici> Methanobacterium formicicum DSM 1312' : 0.03067 , '<Mt.fervid1> Methanothermus fervidus' : 0.19624 ) : 0.01978 ) : 0.0947 , '<Tc.celer> Thermococcus celer str. VU 13 DSM 2476 (T)' : 0.00981 ) : 0.05532 , ('<Mc.vanniel> Methanococcus vannielii str. EY33' : 0.02484 , '<Mc.jannasc> Methanococcus jannaschii str. JAL-1 DSM 2661 (T)' : 0.1614 ) : 0.00857 ) : 0.02807 , '<Mpy.kandl1> Methanopyrus kandleri str. av19 DSM 6324 (T)' : 0.09845 ) : 0.02703 , ('<env.pJP27> Mud Volcano area of Yellowstone NP ("Black Pool") hot spring DNA clone pJP27' : 0.06783 , (('<env.SBAR12> Santa Barbara Channel bacterioplankton DNA clone SBAR12' : 0.1046 , '<env.pJP89> Mud Volcano area of Yellowstone NP ("Black Pool") hot spring DNA clone pJP89' : 0.28523 ) : 0.01132 , ('<Tmf.penden> Thermofilum pendens str. Hvv3 DSM 2475 (T)' : 0.04404 , ('<Sul.acalda> Sulfolobus acidocaldarius str. 98-3 ATCC 33909 (T)' : 0.04024 , '<Thp.tenax> Thermoproteus tenax' : 0.15875 ) : 0.02106 ) : 0.09273 ) : 0.20883 ) : 0.03789 ) : 0.31178 , ('<Aqu.pyroph> Aquifex pyrophilus str. Kol5a' : 0.20649 , (('<Tt.maritim> Thermotoga maritima str. MSB8 DSM 3109 (T)' : 0.01001 , '<Fer.island> Fervidobacterium islandicum str. H-21 DSM 5733 (T)' : 0.16351 ) : 0.23062 , ((('<Mei.ruber4> Meiothermus ruber str. Loginova 21 ATCC 35948 (T)' : 0.14908 , '<D.radiodur> Deinococcus radiodurans ATCC 35073' : 0.19907 ) : 0.08298 , ('<Cfx.aurant> Chloroflexus aurantiacus str. J-10-fl ATCC 29366 (T)' : 0.1976 , '<Tmc.roseum> Thermomicrobium roseum ATCC 27502 (T)' : 0.36297 ) : 0.11213 ) : 0.01165 , (((((((((('<Acp.laidla> Acholeplasma laidlawii str. JA1' : 0.11002 , '<C.ramosum> Clostridium ramosum str. 113-I ATCC 25582 (T)' : 0.30774 ) : 0.00736 , '<M.capricol> Mycoplasma capricolum ATCC 27343 (T) [gene=rrnB]' : 0.38452 ) : 0.10528 , '<Stc.therm3> Streptococcus thermophilus DSM 20617 (T)' : 0.05073 ) : 0.15065 , '<Eco.faecal> Enterococcus faecalis' : 0.0306 ) : 0.01738 , ('<L.casei> Lactobacillus casei subsp. casei ATCC 393 (T)' : 0.13937 , '<L.delbruck> Lactobacillus delbrueckii subsp. delbrueckii str. Calvert ATCC 9649 (T)' : 0.04809 ) : 0.01852 ) : 0.02217 , '<Lis.monoc3> Listeria monocytogenes' : 0.02418 ) : 0.0404 , '<B.cereus4> Bacillus cereus IAM 12605 (T)' : 0.06989 ) : 0.0034 , ('<B.subtilis> Bacillus subtilis str. 168' : 0.05051 , '<B.stearoth> Bacillus stearothermophilus NCDO 1768 (T)' : 0.05959 ) : 0.0075 ) : 0.12658 , '<Eub.barker> Eubacterium barkeri ATCC 25849 (T)' : 0.28781 ) : 0.0097 , ('<C.quercico> Clostridium quercicolum ATCC 25974 (T)' : 0.13519 , '<Hel.chlor2> Heliobacterium chlorum ATCC 35205 (T)' : 0.1075 ) : 0.01024 ) : 0.01183 , ('<Fus.nuclea> Fusobacterium nucleatum subsp. nucleatum ATCC 25586 (T)' : 0.08593 , ('<Stm.ambofa> Streptomyces ambofaciens' : 0.06051 , ('<Cor.xerosi> Corynebacterium xerosis ATCC 373 (T)' : 0.10315 , ('<Bif.bifidu> Bifidobacterium bifidum ATCC 29521 (T)' : 0.29842 , '<Arb.globif> Arthrobacter globiformis str. 168 DSM 20124 (T)' : 0.12957 ) : 0.06797 ) : 0.00748 ) :

Docket 010AUS; USSN 10/057,270; Figure 10A-10C The representative prokaryotic phylogenetic tree in Newick format.

Figure 10B

0.3137 ) ; 0.01738 ) ; 0.00511 , ('<C.leptum> Clostridium leptum ATCC 29065 (T)' ; 0.16126 , ('<C.butyric4> Clostridium butyricum str. E.VI.3,6,1 NCIMB 8082' ; 0.06037 , '<C.pasteuri> Clostridium pasteurianum ATCC 6013 (T)' ; 0.07626 ) ; 0.38023 ) ; 0.02432 ) ; 0.01262 , (((((((('<Rub.gelat2> Rubrivivax gelatinosus str. ATH 2.2.1 ATCC 17011 (T)' ; 0.07169 , '<Spr.voluta> Spirillum volutans ATCC 19554 (T)' ; 0.06661 ) ; 0.00462 , '<Rcy.purpur> Rhodocyclus purpureus str. 6770 DSM 168 (T)' ; 0.04015 ) ; 0.02165 , '<Nis.gonor1> Neisseria gonorrhoeae str. B 5025 NCTC 8375 (T)' ; 0.19789 ) ; 0.01431 , '<Ste.maltop> Stenotrophomonas maltophilia ATCC 13637 (T)' ; 0.24098 ) ; 0.02299 , ('<E.coli> Escherichia coli [gene=rrnB operon]' ; 0.05825 , '<Ps.aerugi3> Pseudomonas aeruginosa DSM 50071 (T)' ; 0.63646 ) ; 0.03524 ) ; 0.04488 , '<Alm.vinosm> Allochromatium vinosum ATCC 17899 (T)' ; 0.0233 ) ; 0.04869 , '<Hrh.halch2> Halorhodospira halochloris str. A ATCC 35916 (T)' ; 0.05948 ) ; 0.08019 , (('<R.rubrum3> Rhodospirillum rubrum str. ATH 1.1.1; S.1 ATCC 11170 (T)' ; 0.04904 , '<Azs.brasi2> Azospirillum brasilense str. Sp 7 NCIMB 11860 (T)' ; 0.3086 ) ; 0.01343 , (('<Ric.prowaz> Rickettsia prowazekii str. Breinl ATCC VR-142 (T) (alpha purple bacterium)' ; 0.1406 , '<Spg.capsul> Sphingomonas capsulata ATCC 14666 (T)' ; 0.13872 ) ; 0.02068 , ('<Rhb.legum8> Rhizobium leguminosarum IAM 12609 (T)' ; 0.01576 , ('<Bdr.japoni> Bradyrhizobium japonicum LMG 6138 (T)' ; 0.05736 , '<Rm.vanniel> Rhodomicrobium vannielii str. EY33 ATCC 51194' ; 0.093 ) ; 0.04263 ) ; 0.00617 ) ; 0.03466 ) ; 0.06772 ) ; 0.00546 , (('<Myx.xanthu> Myxococcus xanthus str. DK1622' ; 0.11263 , '<Dsb.postga> Desulfobacter postgatei str. 2 ac 9 DSM 2034 (T)' ; 0.19098 ) ; 0.01154 , ('<Dsv.desulf> Desulfovibrio desulfuricans subsp. desulfuricans ATCC 27774' ; 0.01563 , ('<Bde.stolpi> Bdellovibrio stolpii str. UKi2 ATCC 27052 (T)' ; 0.05967 , ('<Cam.jejun5> Campylobacter jejuni subsp. jejuni str. TGH 9011 ATCC 43431' ; 0.01753 , ('<Wln.succi2> Wolinella succinogenes str. 602W (FDC) ATCC 29543 (T)' ; 0.05551 , '<Hlb.pylor6> Helicobacter pylori ATCC 43504 (T)' ; 0.02351 ) ; 0.18884 ) ; 1.11671 ) ; 0.18947 ) ; 0.01602 ) ; 0.15633 ) ; 0.01513 , (((((('<Trp.pallid> Treponema pallidum str. Nichols' ; 0.14543 , '<Spi.stenos> Spirochaeta stenostrepta str. Z1 ATCC 25083 (T)' ; 0.03623 ) ; 0.03698 , '<Bor.burgdo> Borrelia burgdorferi str. B31 ATCC 35210 (T)' ; 0.3604 ) ; 0.0859 , '<Spi.haloph> Spirochaeta halophila str. RS1 ATCC 29478 (T)' ; 0.02473 ) ; 0.01206 , '<Brs.hyodys> Brachyspira hyodysenteriae str. B204 ATCC 31212' ; 0.43546 ) ; 0.04129 , ('<Lpn.illini> Leptonema illini str. 3055' ; 0.07041 , '<Lps.interK> Leptospira interrogans str. Kennewicki, serovar pomona' ; 0.16902 ) ; 0.05013 ) ; 0.01817 , ('<Fib.sucS85> Fibrobacter succinogenes subsp. succinogenes str. S85 ATCC 19169 (T)' ; 0.23142 , '<Acbt.capsl> Acidobacterium capsulatum str. 161' ; 0.21099 ) ; 0.03073 ) ; 0.0094 , (((('<Syn.6301> Synechococcus sp. PCC 6301' ; 0.12285 , '<Nost.muscr> Nostoc muscorum PCC 7120' ; 0.06977 ) ; 0.01225 , ('<Zea_mays_C> Zea mays (maize; corn; Indian corn) -- chloroplast' ; 0.145 , '<Olst.lut_C> Olisthodiscus luteus (stramenopile) -- chloroplast' ; 0.3525 ) ; 0.09491 ) ; 0.012 , '<Glb.violac> Gloeobacter violaceus PCC 7421' ; 0.07279 ) ; 0.01171 , ('<env.MC18> Mount Coot-tha region (Brisbane, Australia) 5-10cm depth soil DNA clone MC 18' ; 0.01409 , ('<Chd.psitta> Chlamydophila psittaci str. 6BC ATCC VR-125 (T)' ; 0.36004 , '<Pir.staley> Pirellula staleyi ATCC 27377' ; 0.34247 ) ; 0.25993 ) ; 0.1121 ) ; 0.03258 , ('<Chl.limico> Chlorobium limicola str. 8327' ; 0.1389 , ('<Tnm.lapsum> Thermonema lapsum ATCC

Docket 010AUS; USSN 10/057,270; Figure 10A-10C The representative prokaryotic phylogenetic tree in Newick format.

43542 (T)' : 0.0332 , ('<Flx.litora> Flexibacter litoralis str. Lewin SIO-4 ATCC 23117 (T)' : 0.01576 , ('<Cy.hutchin> Cytophaga hutchinsonii str. D465 (P.H.A. Sneath) ATCC 33406 (T)' : 0.0073 , ('<Prb.difflu>
Figure 10C
Persicobacter diffluens str. Lewin LIM-1 ATCC 23140' : 0.00585 , ('<Sap.grandi> Saprospira grandis ATCC 23119 (T)' : 0.02768 , ('<Flx.canada> Flexibacter canadensis ATCC 29591 (T)' : 0.03254 , (('<Bac.fragil> Bacteroides fragilis ATCC 25285 (T)' : 0.04826 , '<Prv.rumcol> Prevotella ruminicola subsp. ruminicola ATCC 19189 (T)' : 0.20539 ) : 0.02821 , ('<Cy.lytica> Cytophaga lytica str. LIM-21 ATCC 23178 (T)' : 0.14365 , '<Emb.brevi2> Empedobacter brevis ATCC 14234' : 0.0913 ) : 0.35994 ) : 0.12199 ) : 0.33291 ) : 0.47588 ) : 0.14622 ) : 0.18424 ) : 0.08878 ) : 0.30465 ) : 0.05104 ) : 0.00825 ) : 0.02261 ) : 0.00329 ) : 0.56238 ) : 0.52312 ) : 0.05444 ) : 0.31178 ); Docket 010AUS; USSN 10/057,270; Figure 10A-10C The representative prokaryotic phylogenetic tree in Newick format.

SEQUENCE LISTING

```
<160> NUMBER OF SEQ ID NOS: 54

<210> SEQ ID NO 1
<211> LENGTH: 15
<212> TYPE: RNA
<213> ORGANISM: Unknown
<220> FEATURE:
<223> OTHER INFORMATION: sequence composed of several organisms

<400> SEQUENCE: 1
aaaaaaacag ucuca                                                     15

<210> SEQ ID NO 2
<211> LENGTH: 15
<212> TYPE: RNA
<213> ORGANISM: Unknown
<220> FEATURE:
<223> OTHER INFORMATION: sequence composed of several organisms

<400> SEQUENCE: 2
aaaaaaacag ucuca                                                     15

<210> SEQ ID NO 3
<211> LENGTH: 15
<212> TYPE: RNA
<213> ORGANISM: Unknown
<220> FEATURE:
<223> OTHER INFORMATION: sequence composed of several organisms

<400> SEQUENCE: 3
aaaaaaacag ucuca                                                     15

<210> SEQ ID NO 4
<211> LENGTH: 15
<212> TYPE: RNA
<213> ORGANISM: Unknown
<220> FEATURE:
<223> OTHER INFORMATION: sequence composed of several organisms

<400> SEQUENCE: 4
aaaaaaacag ucuca                                                     15

<210> SEQ ID NO 5
```

```
<211> LENGTH: 15
<212> TYPE: RNA
<213> ORGANISM: Unknown
<220> FEATURE:
<223> OTHER INFORMATION: sequence composed of several organisms

<400> SEQUENCE: 5
aaaaaaacag ucuca                                                    15

<210> SEQ ID NO 6
<211> LENGTH: 15
<212> TYPE: RNA
<213> ORGANISM: Unknown
<220> FEATURE:
<223> OTHER INFORMATION: sequence composed of several organisms

<400> SEQUENCE: 6
aaaaaaagac gguac                                                    15

<210> SEQ ID NO 7
<211> LENGTH: 15
<212> TYPE: RNA
<213> ORGANISM: Unknown
<220> FEATURE:
<223> OTHER INFORMATION: sequence composed of several organisms

<400> SEQUENCE: 7
aaaaaaagac gguac                                                    15

<210> SEQ ID NO 8
<211> LENGTH: 15
<212> TYPE: RNA
<213> ORGANISM: Unknown
<220> FEATURE:
<223> OTHER INFORMATION: sequence composed of several organisms

<400> SEQUENCE: 8
aaaaaaagac gguac                                                    15

<210> SEQ ID NO 9
<211> LENGTH: 15
<212> TYPE: RNA
<213> ORGANISM: Unknown
<220> FEATURE:
<223> OTHER INFORMATION: sequence composed of several organisms

<400> SEQUENCE: 9
aaaaaaagac gguac                                                    15

<210> SEQ ID NO 10
<211> LENGTH: 15
<212> TYPE: RNA
<213> ORGANISM: Unknown
<220> FEATURE:
<223> OTHER INFORMATION: sequence composed of several organisms

<400> SEQUENCE: 10
aaaaaaagac gguac                                                    15

<210> SEQ ID NO 11
<211> LENGTH: 15
<212> TYPE: RNA
<213> ORGANISM: Unknown
<220> FEATURE:
<223> OTHER INFORMATION: sequence composed of several organisms

<400> SEQUENCE: 11
```
aaaaaaauga cggua    15

<210> SEQ ID NO 12
<211> LENGTH: 15
<212> TYPE: RNA
<213> ORGANISM: Unknown
<220> FEATURE:
<223> OTHER INFORMATION: sequence composed of several organisms

<400> SEQUENCE: 12
aaaaaaauga cggua    15

<210> SEQ ID NO 13
<211> LENGTH: 15
<212> TYPE: RNA
<213> ORGANISM: Unknown
<220> FEATURE:
<223> OTHER INFORMATION: sequence composed of several organisms

<400> SEQUENCE: 13
aaaaaaauga cggua    15

<210> SEQ ID NO 14
<211> LENGTH: 15
<212> TYPE: RNA
<213> ORGANISM: Unknown
<220> FEATURE:
<223> OTHER INFORMATION: sequence composed of several organisms

<400> SEQUENCE: 14
aaaaaaauga cggua    15

<210> SEQ ID NO 15
<211> LENGTH: 15
<212> TYPE: RNA
<213> ORGANISM: Unknown
<220> FEATURE:
<223> OTHER INFORMATION: sequence composed of several organisms

<400> SEQUENCE: 15
aaaaaaauga cggua    15

<210> SEQ ID NO 16
<211> LENGTH: 15
<212> TYPE: RNA
<213> ORGANISM: Unknown
<220> FEATURE:
<223> OTHER INFORMATION: sequence composed of several organisms

<400> SEQUENCE: 16
aaaaaacagu cucag    15

<210> SEQ ID NO 17
<211> LENGTH: 15
<212> TYPE: RNA
<213> ORGANISM: Unknown
<220> FEATURE:
<223> OTHER INFORMATION: sequence composed of several organisms

<400> SEQUENCE: 17
aaaaaacagu cucag    15

<210> SEQ ID NO 18
<211> LENGTH: 15
<212> TYPE: RNA
<213> ORGANISM: Unknown
<220> FEATURE:

-continued

<223> OTHER INFORMATION: sequence composed of several organisms

<400> SEQUENCE: 18
aaaaaacagu cucag                                                    15

<210> SEQ ID NO 19
<211> LENGTH: 15
<212> TYPE: RNA
<213> ORGANISM: Unknown
<220> FEATURE:
<223> OTHER INFORMATION: sequence composed of several organisms

<400> SEQUENCE: 19
aaaaaacagu cucag                                                    15

<210> SEQ ID NO 20
<211> LENGTH: 15
<212> TYPE: RNA
<213> ORGANISM: Unknown
<220> FEATURE:
<223> OTHER INFORMATION: sequence composed of several organisms

<400> SEQUENCE: 20
aaaaaacagu cucag                                                    15

<210> SEQ ID NO 21
<211> LENGTH: 12
<212> TYPE: RNA
<213> ORGANISM: M.mycoides
<220> FEATURE:
<223> OTHER INFORMATION: Organism specific sequences

<400> SEQUENCE: 21
aaaaaaacca gu 12

<210> SEQ ID NO 22
<211> LENGTH: 12
<212> TYPE: RNA
<213> ORGANISM: Unknown
<220> FEATURE:
<223> OTHER INFORMATION: source could not be determined

<400> SEQUENCE: 22
aaaaaaacgu gc 12

<210> SEQ ID NO 23
<211> LENGTH: 12
<212> TYPE: RNA
<213> ORGANISM: Unknown
<220> FEATURE:
<223> OTHER INFORMATION: source could not be determined

<400> SEQUENCE: 23
aaaaaaaguu uc 12

<210> SEQ ID NO 24
<211> LENGTH: 12
<212> TYPE: RNA
<213> ORGANISM: Unknown
<220> FEATURE:
<223> OTHER INFORMATION: source could not be determined

<400> SEQUENCE: 24
aaaaaaauaa aa 12

<210> SEQ ID NO 25

```
<211> LENGTH: 12
<212> TYPE: RNA
<213> ORGANISM: Unknown
<220> FEATURE:
<223> OTHER INFORMATION: source could not be determined

<400> SEQUENCE: 25
aaaaaaauga ag                                                          12

<210> SEQ ID NO 26
<211> LENGTH: 12
<212> TYPE: RNA
<213> ORGANISM: Unknown
<220> FEATURE:
<223> OTHER INFORMATION: source could not be determined

<400> SEQUENCE: 26
aaaaaaauua gg                                                          12

<210> SEQ ID NO 27
<211> LENGTH: 12
<212> TYPE: RNA
<213> ORGANISM: Unknown
<220> FEATURE:
<223> OTHER INFORMATION: source could not be determined

<400> SEQUENCE: 27
aaaaaaauuu au                                                          12

<210> SEQ ID NO 28
<211> LENGTH: 12
<212> TYPE: RNA
<213> ORGANISM: Unknown
<220> FEATURE:
<223> OTHER INFORMATION: source could not be determined

<400> SEQUENCE: 28
aaaaaacacg uc                                                          12

<210> SEQ ID NO 29
<211> LENGTH: 12
<212> TYPE: RNA
<213> ORGANISM: Unknown
<220> FEATURE:
<223> OTHER INFORMATION: source could not be determined

<400> SEQUENCE: 29
aaaaaaccaa cc                                                          12

<210> SEQ ID NO 30
<211> LENGTH: 12
<212> TYPE: RNA
<213> ORGANISM: Unknown
<220> FEATURE:
<223> OTHER INFORMATION: source could not be determined

<400> SEQUENCE: 30
aaaaaaccaa uc                                                          12

<210> SEQ ID NO 31
<211> LENGTH: 12
<212> TYPE: RNA
<213> ORGANISM: B.pallidus
<220> FEATURE:
<223> OTHER INFORMATION: Organism specific sequences

<400> SEQUENCE: 31
```
aaaaaaccac uc					12

<210> SEQ ID NO 32
<211> LENGTH: 12
<212> TYPE: RNA
<213> ORGANISM: Unknown
<220> FEATURE:
<223> OTHER INFORMATION: source could not be determined

<400> SEQUENCE: 32
aaaaaacccu uc					12

<210> SEQ ID NO 33
<211> LENGTH: 12
<212> TYPE: RNA
<213> ORGANISM: Unknown
<220> FEATURE:
<223> OTHER INFORMATION: source could not be determined

<400> SEQUENCE: 33
aaaaaaccgg cc					12

<210> SEQ ID NO 34
<211> LENGTH: 12
<212> TYPE: RNA
<213> ORGANISM: Unknown
<220> FEATURE:
<223> OTHER INFORMATION: source could not be determined

<400> SEQUENCE: 34
aaaaaaccgg uc					12

<210> SEQ ID NO 35
<211> LENGTH: 12
<212> TYPE: RNA
<213> ORGANISM: Unknown
<220> FEATURE:
<223> OTHER INFORMATION: source could not be determined

<400> SEQUENCE: 35
aaaaaacgug cc					12

<210> SEQ ID NO 36
<211> LENGTH: 12
<212> TYPE: RNA
<213> ORGANISM: Unknown
<220> FEATURE:
<223> OTHER INFORMATION: source could not be determined

<400> SEQUENCE: 36
aaaaaacuaa ag					12

<210> SEQ ID NO 37
<211> LENGTH: 12
<212> TYPE: RNA
<213> ORGANISM: Unknown
<220> FEATURE:
<223> OTHER INFORMATION: source could not be determined

<400> SEQUENCE: 37
aaaaaacucu gc					12

<210> SEQ ID NO 38
<211> LENGTH: 12
<212> TYPE: RNA
<220> FEATURE:

-continued

<223> OTHER INFORMATION: source could not be determined

<400> SEQUENCE: 38
aaaaaacuga cg                                                              12

<210> SEQ ID NO 39
<211> LENGTH: 12
<212> TYPE: RNA
<213> ORGANISM: Unknown
<220> FEATURE:
<223> OTHER INFORMATION: source could not be determined

<400> SEQUENCE: 39
aaaaaagaag ca                                                              12

<210> SEQ ID NO 40
<211> LENGTH: 12
<212> TYPE: RNA
<213> ORGANISM: Unknown
<220> FEATURE:
<223> OTHER INFORMATION: source could not be determined

<400> SEQUENCE: 40
aaaaaagagu gg                                                              12

<210> SEQ ID NO 41
<211> LENGTH: 12
<212> TYPE: RNA
<213> ORGANISM: Unknown
<220> FEATURE:
<223> OTHER INFORMATION: source could not be determined

<400> SEQUENCE: 41
aaaaaagccc ac                                                              12

<210> SEQ ID NO 42
<211> LENGTH: 12
<212> TYPE: RNA
<213> ORGANISM: Unknown
<220> FEATURE:
<223> OTHER INFORMATION: source could not be determined

<400> SEQUENCE: 42
aaaaaagccg uc                                                              12

<210> SEQ ID NO 43
<211> LENGTH: 12
<212> TYPE: RNA
<213> ORGANISM: Unknown
<220> FEATURE:
<223> OTHER INFORMATION: source could not be determined

<400> SEQUENCE: 43
aaaaaagccu ua                                                              12

<210> SEQ ID NO 44
<211> LENGTH: 12
<212> TYPE: RNA
<213> ORGANISM: Unknown
<220> FEATURE:
<223> OTHER INFORMATION: source could not be determined

<400> SEQUENCE: 44
aaaaaagggg ga                                                              12

<210> SEQ ID NO 45

```
<211> LENGTH: 12
<212> TYPE: RNA
<213> ORGANISM: Unknown
<220> FEATURE:
<223> OTHER INFORMATION: source could not be determined

<400> SEQUENCE: 45
aaaaaaguug uc                                                              12

<210> SEQ ID NO 46
<211> LENGTH: 12
<212> TYPE: RNA
<213> ORGANISM: Unknown
<220> FEATURE:
<223> OTHER INFORMATION: source could not be determined

<400> SEQUENCE: 46
aaaaaaguuu cg                                                              12

<210> SEQ ID NO 47
<211> LENGTH: 12
<212> TYPE: RNA
<213> ORGANISM: Unknown
<220> FEATURE:
<223> OTHER INFORMATION: source could not be determined

<400> SEQUENCE: 47
aaaaaauaaa ac                                                              12

<210> SEQ ID NO 48
<211> LENGTH: 12
<212> TYPE: RNA
<213> ORGANISM: Unknown
<220> FEATURE:
<223> OTHER INFORMATION: source could not be determined

<400> SEQUENCE: 48
aaaaaauacu cc                                                              12

<210> SEQ ID NO 49
<211> LENGTH: 12
<212> TYPE: RNA
<213> ORGANISM: Unknown
<220> FEATURE:
<223> OTHER INFORMATION: source could not be determined

<400> SEQUENCE: 49
aaaaaauaga gu                                                              12

<210> SEQ ID NO 50
<211> LENGTH: 12
<212> TYPE: RNA
<213> ORGANISM: Unknown
<220> FEATURE:
<223> OTHER INFORMATION: source could not be determined

<400> SEQUENCE: 50
aaaaaauaug uc                                                              12

<210> SEQ ID NO 51
<211> LENGTH: 12
<212> TYPE: RNA
<213> ORGANISM: Unknown
<220> FEATURE:
<223> OTHER INFORMATION: source could not be determined

<400> SEQUENCE: 51
```

```
aaaaaaucaa aa                                                              12

<210> SEQ ID NO 52
<211> LENGTH: 12
<212> TYPE: RNA
<213> ORGANISM: Unknown
<220> FEATURE:
<223> OTHER INFORMATION: source could not be determined

<400> SEQUENCE: 52
aaaaaaucaa au                                                              12

<210> SEQ ID NO 53
<211> LENGTH: 12
<212> TYPE: RNA
<213> ORGANISM: Unknown
<220> FEATURE:
<223> OTHER INFORMATION: source could not be determined

<400> SEQUENCE: 53
aaaaaaucaa uc                                                              12

<210> SEQ ID NO 54
<211> LENGTH: 12
<212> TYPE: RNA
<213> ORGANISM: Unknown
<220> FEATURE:
<223> OTHER INFORMATION: source could not be determined

<400> SEQUENCE: 54
aaaaaaucca uc                                                              12
```

METHODS FOR DETERMINING THE GENETIC AFFINITY OF MICROORGANISMS AND VIRUSES

CROSS-REFERENCES TO RELATED APPLICATIONS

This Application claims priority of provisional application 60/264,403 filed Jan. 26, 2001.

Applicants expressly incorporate by reference the CRF Sequence Listing 010AUS.txt of 2 KB which was created Jan. 25, 2012.

STATEMENT REGARDING FEDERALLY SPONSORED RESEARCH OR DEVELOPMENT

The research was funded in part by grants to R.C.W. and G.E.F. from NASA through the National Space Biomedical Research Institute.

RESULTS CD APPENDIX

Certain results obtained by the invention are set forth on the CD which is enclosed as a part of the application under 37 Code of Federal Regulations Section 1.58.

PROGRAM CODE APPENDIX

The computer programs and subroutines of the invention are set forth on the CD, which is enclosed as a part of the application under 37 Code of Federal Regulations Section 1.96.

ASCII, MS Windows;

| Name | Size | Type | Created Time |
|---|---|---|---|
| Programs | | File Folder | Jan. 24, 2002 6:02 PM |
| \|-> calc_node_values | 6 KB | Text Document | Jan. 23, 2002 6:35 PM |
| \|-> fasta2flat | 2 KB | Text Document | Jan. 23, 2002 6:35 PM |
| \|-> group_node_lister | 4 KB | Text Document | Jan. 23, 2002 6:35 PM |
| \|-> hybridize | 3 KB | Text Document | Jan. 23, 2002 6:35 PM |
| \|-> list_hit_branch_nodes | 5 KB | Text Document | Jan. 23, 2002 6:35 PM |
| \|-> probes_hash_table_generator | 6 KB | Text Document | Jan. 23, 2002 6:35 PM |
| \|-> result_printer | 5 KB | Text Document | Jan. 23, 2002 6:35 PM |
| \|-> result_printer_ | 6 KB | Text Document | Jan. 23, 2002 6:35 PM |
| \|-> select_seq | 3 KB | Text Document | Jan. 23, 2002 6:35 PM |
| \|-> seq_classifier | 2 KB | Text Document | Jan. 23, 2002 6:35 PM |
| \\-> tree_parser | 16 KB | Text Document | Jan. 23, 2002 6:35 PM |
| signature_sequences | | File Folder | Jan. 24, 2002 6:02 PM |
| \|-> 10_mers.txt | 12,552 KB | Text Document | Jan. 23, 2002 6:26 PM |
| \|-> 11_mers.txt | 13.611 KB | Text Document | Jan. 23, 2002 6:28 PM |
| \|-> 12_mers.txt | 14,636 KB | Text Document | Jan. 23, 2002 6:28 PM |
| \|-> 13_mers.txt | 15,690 KB | Text Document | Jan. 23, 2002 6:30 PM |
| \|-> 15_mers.txt | 17,790 KB | Text Document | Jan. 23, 2002 6:31 PM |
| \|-> 5_mers.txt | 146 KB | Text Document | Jan. 23, 2002 6:31 PM |
| \|-> 6_mers.txt | 598 KB | Text Document | Jan. 23, 2002 6:32 PM |
| \|-> 7_mers.txt | 2,332 KB | Text Document | Jan. 23, 2002 6:32 PM |
| \|-> 8_mers.txt | 6,763 KB | Text Document | Jan. 23, 2002 6:33 PM |
| \|-> 9_mers.txt | 10,781 KB | Text Document | Jan. 23, 2002 6:23 PM |
| \|-> representative_tree_16S.txt | 212 KB | Text Document | Jan. 23, 2002 6:26 PM |
| \|-> unique_12_mers.txt | 3,815 KB | Text Document | Jan. 23, 2002 6:34 PM |
| Copyright.txt | 1 KB | Text Document | Jan. 23, 2002 6:47 PM |

COPYRIGHT

Contained herein is material that is subject to international copyright protection. The copyright owner has no objection to the facsimile reproduction of the patent disclosure by any person as it appears in the Patent and Trademark files or records, but otherwise reserves all rights to the copyright whatsoever.

BACKGROUND OF THE INVENTION

I. Field of the Invention

The present invention relates to the general field if biochemical assays and separations, and to apparatus for their practice, generally classified in U.S. Patent Class 435/6.

II. Description of the Prior Art

Unlike multicellular organisms, bacteria and simple eukaryotic microorganisms have very limited morphological diversity and typically do not leave a significant fossil record. It therefore was initially very difficult to develop a classification system, which reflects actual genetic relationship. Instead, classic bacterial taxonomic methods, such as morphology and carbon source utilization were used to classify bacteria in a deterministic way. The goal was to develop a hierarchy of tests that ultimately could reproducibly assign a consistent name to an unknown isolate. When organisms gave very similar results on the various tests they would ultimately be assigned to the same species regardless of actual genetic relationship. Thus, organisms were sometimes grouped together that were fundamentally very different.

This situation changed dramatically in the 1970's due to the pioneering work of Carl Woese and his colleagues. In order to obtain a genotypic classification, methods based on molecular sequence analysis of ribosomal RNA (rRNA) were developed. The rRNAs offered the advantage of being found in all organisms and the equivalent molecules could be readily isolated and purified from essentially any organism. The large ribosomal RNAs vary in length depending on the organism and therefore have different names, e.g. 16S rRNA, 18S rRNA etc, depending on the organism under consideration. To avoid this difficulty, the terminology small subunit RNA (SSU RNA) and large subunit RNA (LSU RNA) is used to specify any of the RNAS belonging to each class. Among the rRNAs, 5S rRNA with approximately 120 nucleotides was thought to be too short to be useful and the LSU RNA, (23S rRNA in bacteria), would have been far more difficult to work with. Attention therefore focused on the SSU RNA (16S rRNA in bacteria). 16S rRNA is a major component of the bacterial small ribosomal subunit. It consists of approximately 1,550 ribonucleotides in *Escherichia coli* and has an intricate secondary structure featuring extensive intrachain base pairing. The detailed three-dimensional folding of 16S rRNA in the *Thermus aquaticus* 30S ribosomal subunit has recently been determined by X-ray crystallography. As a major component of the ribosome, 16S rRNA interacts with 23S rRNA to establish the overall geometry of the ribosome and is directly involved in the initiation of protein biosynthesis by ribosomes.

When Woese first began using 16S rRNA in his evolutionary studies it was not technically feasible to sequence the entire RNA. Therefore a characterization approach was developed (Uchida et al., 1974) in which the 16S rRNA was fragmented by the nuclease, ribonuclease $T_1$. This enzyme cleaves the RNA at guanosine (G) residues and thereby reduced the RNA to a collection of fragments of various lengths with a single terminal G. The non-G portion of the fragment was then sequenced. The lists of all such fragments obtained from a single RNA was referred to as a catalog. Catalogs of ribonuclease $T_1$ fragments from 16S rRNAs isolated from a variety of organisms were compared to one another and cluster analysis was used to construct a tree of relationship between the various bacteria (Fox et al., 1977). By 1980, enough data of this type had accumulated that it was possible to construct the first trees that seriously attempted to identify the actual historical relationships between the various types of bacteria (Fox et al., 1980; Woese, 1987).

Later, as sequencing technology was improved, it became possible to sequence and compare entire 16S rRNAs.

In an effort to better understand the tree produced by cluster analysis, an alternative means of examining relationships known as "signature analysis" was developed (Woese et al., 1980). It was observed that certain of the ribonuclease $T_1$ fragments were only found in a subset of the 16S rRNA catalogs. Frequently there was more than one such sequence that was uniquely found in the same group of organisms. Thus, the term "signature" was introduced as follows: "a set of oligonucleotides that is characteristic of (unique to) a group of organisms defines that group and is a "signature" for the group". These signatures suggested that there was a relationship between the organisms in the group and so the tree was examined to see if the tree-generating algorithm had in fact found the expected relationship.

This process of checking the reasonableness of trees produced from the cataloging data was employed on several occasions (Woese et al., 1980; Woese et al., 1984; McGill et al., 1986). In its final rendition, (McGill et al., 1986) the notion of a signature quality index that could be calculated for every individual RNAse $T_1$ oligonucleotide was introduced as a means of formalizing the extent to which there was or was not a signature for each branch in the tree.

Today, comparison of 16S rRNA sequences is widely used to establish the genetic relationship between bacteria. A typical approach is to amplify and sequence 16S rDNA from various prokaryotic organisms. The resulting sequences are aligned with other 16S rRNA sequences and an appropriate method, e.g. maximum likelihood, is used to construct a tree that reflects likely historical relationships. Several public databases exist containing complete and partial small subunit rRNA sequences. For example, release 8 of the RDP database (Maidak et al., 2000) includes data far the small subunit RNA from over 16,000 bacteria, eukaryotes, plastids and mitochondria.

As Woese's work became well known it began to be appreciated that RNA might be useful in detecting the presence of a target organism in a test sample. Thus, in 1980 Kohne applied for patents (U.S. Pat. No. 4,851,330 granted 25 Jul. 1989 and U.S. Pat. No. 5,288,611 granted Feb. 22, 1994) the essence of which is that a nucleic acid probe that is complementary to the rRNA of a specific target can be used to detect the presence of that target. This core approach has been widely used in microbial identification with probes usually being devised by sequence comparison rather than Kohne's preferred embodiment that was subtractive hybridization. Several commercial products rely on this approach.

The invention described here provides a novel approach for rapidly determining the genetic affinity of organisms in test sample. The invention's methodology is far more general than the specifically targeted tests of the Kohne approach, and faster and more convenient than detailed sequencing of the rRNAs or their encoding DNA. The method of this invention is currently most readily utilized with 16S rRNA sequence data but can be adapted to other data sets such as rRNA spacers, RNAse P RNA, genomic DNA or RNA of viruses, etc. One begins by defining microbial groups within a phylogenetic tree that includes the organism range of interest, e.g. all bacteria for example. Then a set of characteristic oligonucleotides, each of which identifies a group in the phylogenetic tree, is determined according to a newly developed algorithm of the invention. This set of signature oligonucleotides is utilized in a hybridization experiment, e.g. a DNA microarray, the results of which are then used to quickly identify the phylogenetic neighborhood of a problematic bacterium, or other microorganism. These hybridization experiments can be miniaturized so that minimally trained personnel can readily conduct them in difficult environments. The set of signature oligonucleotides can be updated and redesigned as our knowledge of the true genetic affinity between known organisms improves. In many cases, the hybridization array will be able to determine the genetic affinity of multiple organisms in a sample in one experiment. If the organism turns out to be a previously known organism, its identity can be determined to the species level if suitable signature oligonucleotides are included in the hybridization. Under some circumstances, the signature sequences can also be used in assays which detection does not rely on hybridization.

Problem Solved by the Invention

The Kohne patents (below) teach methods to utilize probes to detect specific predetermined organisms or groups of organisms. Thus, the '611 patent teaches us how to determine if a particular species of organism is or is not present in a test sample. The '330 patent teaches us how to detect specific groups of organisms as well as individual organisms. It is somewhat limited, however, in that the probes under this invention are obtained by selection; i.e. subtractive hybridization. Others have subsequently demonstrated the ability to detect specific groups using probes based on sequence comparisons.

It is implicit in all these prior art references that one knows what one is looking for. Thus, a prior art test can be specifically designed for detecting *Legionella*. However, this is not always what is needed, e.g. a quick response might be necessary to respond to an outbreak of a previously unknown transmissible microbial disease. Perhaps even more to the point in this day and age, a terrorist could bioengineer a normally harmless organism to carry a gene that results in production of a deadly toxin. The resulting organism would have properties not normally associated with the bacterium that carries the toxin gene. Indeed, the organism itself might be from a previously unknown genus. Similarly, there are instances where work is done in remote locations such as the Antarctic or on the International Space Station where one has extremely limited diagnostic capability available. Even in standard medical practice microbial identification is needlessly cumbersome in that many alternative specialized tests are now used to identify the presence of the various known pathogens. In all of these cases the ability to genetically characterize and hence identify what organisms or viruses are present in a test sample with a single universal test system would be invaluable. The invention provides this badly needed solution in a very general way.

References

Fox, G E, Pechman, K R, and Woese, C R (1977) Comparative cataloging of 16S Ribosomal Ribonucleic Acid: Molecular Approach to Prokaryotic Systematics. Intn. J. Syst. Bacteriol. 27:44-57 (1977).

Fox G E, Stackebrandt P., Hespel R B, Gibson J, Maniloff J, Dyer T A, Wolfe R S, Balch W E, Tanner R S, Magrum L J, Zablen L B, Blakemore R, Gupta R, Bonen L, Lewis B J, Stahl D A, Luehrsen K R, Chen K N, and Woese C R (1980). The phylogeny of prokaryotes, Science 209: 457-463.

Kohne, David E.; Method for detecting identifying and quantitating organisms and viruses; U.S. Pat. No. 5,288, 611 granted 22 Feb. 1994 which claims: "1. A method for detecting the presence of a species of organism comprising a ribosomal nucleic acid sequence, in a test sample, comprising the steps of: contacting ribosomal nucleic acid from said test sample with a nucleic acid probe able to hybridize to only a portion of said ribosomal nucleic acid sequence of said organism, incubating said probe and said ribosomal nucleic acid obtained from said test sample under specified Kohne, David E.; Method for detection, identification and quantitation of non-viral organisms; U.S. Pat. No. 4,851, 330 granted 25 Jul. 1989 which claims: "A method for detecting the presence in a test sample of any non-viral organisms belonging to a group, said group consisting of at least one but less than all non-viral organisms, which comprises: (a) bringing together any test sample rRNA and a nucleic acid probe, said probe having been selected to be sufficiently complementary to hybridize to one or more rRNA subunit subsequences that are specific to said group of non-viral organisms and to be shorter in length than the rRNA subunit to which said probe hybridizes; (b) incubating the probe and any test sample rRNA under specified hybridization conditions such that said probe hybridizes to the rRNA of said group of non-viral organisms and does not detectably hybridize to rRNA from other non-viral organisms; and, (c) assaying for hybridization of said probe to any test sample rRNA.

Maidak B L, Cole J R, Lilburn T G, Parker C T Jr, Saxman P R, Stredwick J M, Garrity G M, Li B, Olsen G J, Pramanik S, Schmidt T M, and Tiedje J M (2000) The RDP (Ribosomal Database Project) continues. Nucleic Acids Res. 28:173-174.

McGill T R, Jurka J, Sobieski J M, Pickett M H, Woese C R, and Fox G E (1986) Characteristic archaebacterial 16S rRNA oligonucleotides. Syst. Appl. Microbiol. 7:194-197.

Uchida, T., Bonen, L., Schaup, H W, Lewis, B J, Zablen, L., and Woese, C (1974) The use of ribonuclease $U_2$ in RNA Sequence Determination. J. Molec. Evol. 3:63-77.

Woese C R (1987) Bacterial evolution. Microbiol. Rev. 51:221-271.

Woese C R, Maniloff J, and Zablen L B (1980) Phylogenetic analysis of the mycoplasmas. Proc. Natl. Acad. Sci. USA 77:494-498.

Woese C R, Stachebrandt E, Weisburg W G, Paster B J, Madigan M T, Fowler V J, Hahn C M, Blanz P, Gupta R, Nealson K H, and Fox G E (1984) The phylogeny of purple bacteria: the alpha subdivision. System Appl. Microbiol. 5:315-326.

SUMMARY OF THE INVENTION

Applicants' method is summarized as follows:

A. Establish or otherwise obtain a nucleic acid sequence database of the equivalent nucleic acid from a variety of organisms. It is best to quality control the database; selecting sequences, which are complete and lack unknown segments in the region of interest, discarding the rest. Any of a variety of nucleic acid sequences is potentially useful. At present the substantial amount of sequence information available for rRNAs, especially the SSU rRNA (i.e. 16S rRNA in bacteria) makes that molecule an excellent choice for bacteria and eukaryotic microorganisms. In the case of viruses the most promising source of information is currently the sequence of the genomic DNA or RNA.

B. Obtain or develop a bifurcating node phylogenetic tree that substantially reflects the genetic relationships between the organisms or viruses whose sequences are included in the nucleic acid sequence database that is to be used.

C. Choose a smallest sequence length of interest for the characteristic sequence, which will be sought. This length will differ depending in on the length of the nucleic acid molecule or region being examined, the number of sequences in the dataset and various constraints by the experimental systems that will be used.

D. Test all possible sequences of this length N against the entries in the nucleic acid sequence database that is being used in conjunction with the tree. A signature quality function such as Qs is calculated for every possible sequence of length N at each node in the tree. It is preferable and computationally efficient to only calculate the Qs value for test sequences of length N that occur at least twice in the database. Those test sequences that never occur are not signature sequences. Test sequences that occur once are perfect signature sequences of the particular organism or virus from which the nucleic acid was obtained. The signature quality function can be defined in a variety of ways but should be constructed so as to determine the extent to which a test sequence of length N is found in all the organisms in the database belonging to the set of sequences represented by a node in the tree and not found elsewhere. A particular test sequence is determined to be a perfect signature of the organisms represented by a particular bifurcation node on the phylogenetic tree if all the nucleic acid sequences represented by that node contain the sequence and the sequence is not found in any nucleic acid sequence not represented by that node. A value Qs between zero (no signature value) and one (perfect signature) is obtained for each test sequence at each node.

E. Retain as signature sequences those test sequences having $Q_s$ above some criterion. A given node may encompass many signature sequences. Likewise, a particular test sequence can be a signature encompassed by more than one node, though frequently with differing values of Qs. This reflects the child, parent, grandparent, etc. relationship between bifurcation nodes on a phylogenetic tree.

F. Optionally, Repeat the steps D and E for sequences of the desired length (e.g., 7mers, then 8mers, etc).

G. The signature sequences permit the design of hybridization probes for use in an assay. A typical assay can employ a plurality of such signature probes representing at least 50%, and typically more, of the nodes in the applicable phylogenetic tree. The resulting hybridization will allow the identification of the organism's genetic affinity without the necessity of prior knowledge of what it would be. It is contemplated that this invention can allow the development of a single test system that can be used to identify a wide variety of organisms.

H. Once available, the signature sequences can be used in other ways. For example, it is preferable to detect the presence of specific signature sequences in a sample using mass spectrometry. It is also preferable to use signature sequences to design PCR primers for a variety of applications.

In abstract form the invention may be described as follows:

Selecting which sub-sequences in a database of nucleic acid such as 16S rRNA are highly characteristic of particular groupings of bacteria, microorganisms, fungi, etc. on a substantially phylogenetic tree. The invention is also applicable to viruses comprising viral genomic RNA or DNA. A catalogue of highly characteristic signature sequences identified by this method is assembled to establish the genetic identity of an unknown organism. The signature sequences are used to design nucleic acid hybridization probes that include the characteristic sequence or its complement, or are derived from one or more characteristic sequences. A plurality of these signature sequences is used in hybridization to determine the phylogenetic tree position of the organism(s) in a sample. If the target organism is represented in the original sequence database and the signature sequences can identify it to the species or possibly subspecies level. Oligonucleotide arrays of many probes are especially preferred. A hybridization signal can comprise fluorescence, chemiluminescence, or isotopic labeling, etc.; or sequences in a sample can be detected by direct means, e.g. mass spectrometry. The method's characteristic sequences can also be used to design specific PCR primers. The method uniquely identifies the phylogenetic affinity of an unknown organism without requiring prior knowledge of what is present in the sample. Even if the organism has not been previously encountered, the method still provides useful information about which phylogenetic tree bifurcation nodes encompass the organism.

DETAILED DESCRIPTION OF INVENTION

Brief Description of the Several Views of the Drawings

FIG. 2 shows schematically the structure of the composite hash of the oligonucleotides.

FIG. 4 shows schematically how Subsystem I converts the format of the sequence file.

FIG. 10 shows the representative prokaryotic phylogenetic tree in Newick format.

Figure 1:
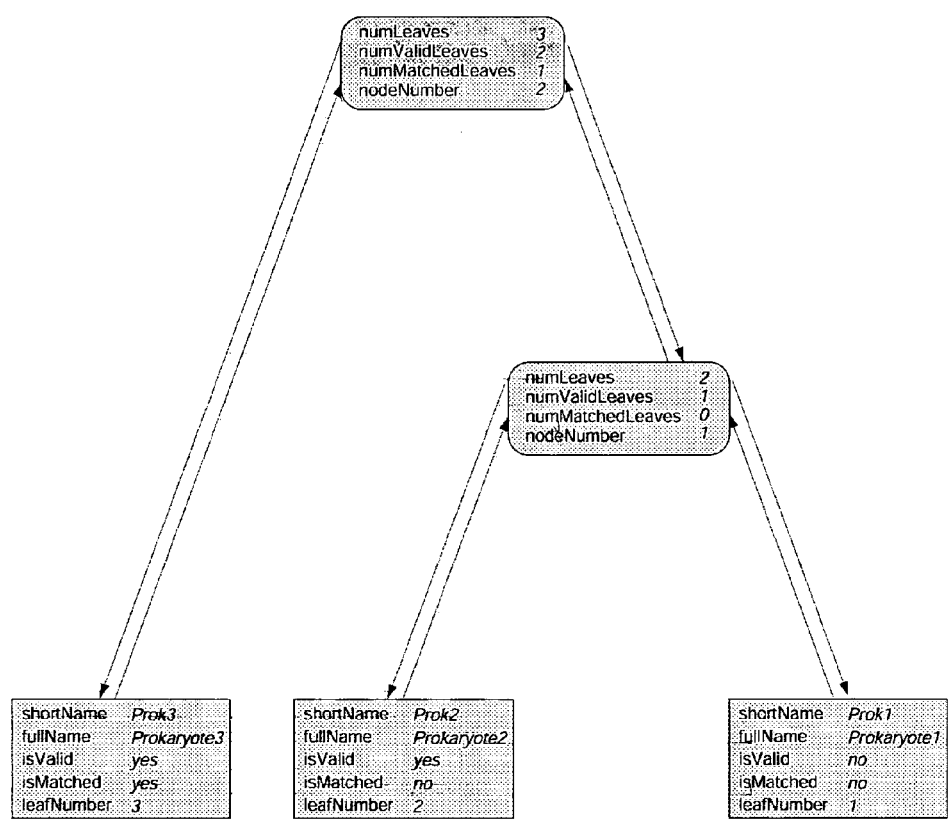
FIG. 1 shows schematically the bi-directional binary tree structure.

Complete lists of this type are on the CD for a several different sequence lengths.

Table B illustrates by example certain information, which is on the CD that is part of this application. The table illustrates signature sequences of length 12 that are completely unique to the organisms that is indicated.

Table C shows the subsystems of the programs used and their functions and components.

Table D shows the numbers of possible oligonucleotides of different lengths

Table E shows a the number of signature sequences that were found at various quality levels as a function of length.

Table F shows the preferred parameters for the invention.

Utility of the Invention

The invention can identify the genetic grouping an unknown organism belongs to even if no perfect match is found for the organism of interest, (the "target"). The invention designs a set of probes that allows one to approximately position any target organism on a tree that displays the genetic relationship between the various organisms. With the invention, it is not necessary to know what organism or group of organisms one is looking for nor is it necessary that it even be previously known to science. Ultimately, even if nothing matches, the invention nonetheless gives useful information. For example, it might be learned that the unknown organism belongs to the group of enteric bacteria but is not any of the known species. Using the invention, it is straightforward to generate a clear file with the five best signature quality values; in the format of Table A. The five best signature quality scores for the indicated sequence are listed with the specific node in the phylogenetic tree.

Unanticipated problems involving microorganisms occur in a variety of settings including space flight, medicine, indoor air quality, bioweapons of mass destruction, epidemics, etc. It would be of value to have a diagnostic system that could readily identify what microorganism is present regardless of prior expectations of what might be found, so as to facilitate a rapid assessment of what is occurring prior to choosing of countermeasures. It is especially essential to determine the genetic identity of the organism that is causing the problem as closely as possible, since this will clarify where the organism came from, what treatments are likely to be effective, etc.

Fortunately, each 16S rRNA sequence contains short sub-sequences that are widely conserved throughout the dataset and despite the fact that there are now over 16,000 publicly available sequences, there are still large numbers of other sub-sequences, which are totally unique to, and hence characteristic of, a particular species or various groups of species that can be identified by methods of the invention. Surprisingly, this pattern of sequence conservation is so strong that it is possible to design specific oligonucleotide hybridization probes that can distinguish individual organisms, and groupings of organisms in a tree of relationship defined by 16S rRNA. Once an appropriate set of target signature sequences have been identified for a desired assay, appropriate probes can be designed. Although it is anticipated that probes based on the signature sequences will be used directly, in some applications, the probes can be modified before use. For example, a "wildcard" base such as inosine might be used to extend or even modify the specificity of a probe. Moreover, two nearby probes might be combined to make a larger probe. Any of a variety of formats can be used to implement the assays. Thus, the final analysis system may utilize PCR-amplified nucleic acids or, because rRNAs are typically present in many thousands of copies per cell, just the sample RNA alone. A variety of detection systems can be used, comprising fluorescence, chemiluminescence and isotopic detection. The resulting assay is highly compatible with hybridization array technology (DNA microarrays), which will allow the simultaneous assay of all the nodes in the underlying tree in one experiment. Thus, it is possible to replace many tests with just one. It is inherent in the prior art that only predetermined microorganisms or groups of microorganisms will be detected. This reflects the fact that prior art assays are based on prior identification of specific probes for the intended application. It is widely believed that a microbial detection system cannot be designed without prior knowledge of what is to be detected. The invention described here implements a novel approach to assay design that overcomes this problem.

Scientific Basis of the Invention

Although the invention is not to be limited by any theory or by the way in which the invention was achieved, the following may be helpful in understanding the invention. An extremely effective approach to determining genetic relatedness among bacteria is to amplify and sequence their 16S rRNA genes (Fox et al., 1980; Woese, 1987). The resulting sequences are aligned with other 16S rRNA sequences and an appropriate method, e.g. maximum likelihood, is used to construct a phylogenetic tree. This process is reasonably fast, very accurate and facilitated by programs and data available via the Internet at the Ribosomal Database Project (RDP) web site http://www.cme.msu.edu/RDP/html/index.html) (Maidak et al., 2000). Many thousands of 16S rRNA sequences, representing essentially all known genera of bacteria, are now available in the RDP and other ribosomal RNA databases. Therefore, when a new isolate of uncertain affiliation is found here on Earth, its genetic identity can be inferred from its placement in the 16S rRNA phylogenetic tree.

It was observed early on in the 1 6S rRNA literature that there were in fact many characteristic ribonuclease T1 (a subset of all possible oligonucleotides that consists only of those which end in G and contain no internal G) "signature" oligonucleotides (Woese et al., 1980;). The existence of such signature oligonucleotides in a set of 16S rRNA sequences actually reflects the fact that certain individual positions have a particular value (i.e. A, C, G or U) in all organisms belonging to a particular cluster and a different value for organisms which do not belong to the cluster. The phylogenetic breadth of the cluster encompassed is different for each signature position and the signatures are typically somewhat noisy in that the characteristic nucleotide is absent in some organisms that belong to the cluster of interest and present in some organisms that are outside the cluster. The information that is carried by these very informative sites is nevertheless precisely what underlies the success of standard algorithms that construct phylogenetic trees.

In order to quantify this information, a signature quality index, which ranges from 0 (no meaningful signature) to 1 (perfect signature) was developed for use with the ribonuclease T1 oligonucleotides (McGill et al., 1986). Such an index allows the quantitative characterization of the utility of any oligonucleotide in determining if an unknown organism belongs to any particular genetic grouping in a particular tree of genetic relatedness. In order to implement the invention it was necessary to modify the signature quality function for use with complete sequence data. The signature quality index used is of the following type:

$$Q_s = ({}^I f_s) \times (1 - {}^O f_s) \tag{1}$$

where $Q_s$ is a measure of signature quality, ${}^I f_s$ is the frequency of the signature sequence within the group under consideration, and ${}^O F_s$ is the frequency of the signature sequence outside the group of interest. The frequencies are based on the number of sequences in the dataset that a particular oligonucleotide matches and the resulting function again varies from 0 (no meaningful signature) to 1 (perfect signature).

To illustrate this function, consider a particular heptamer, which is found in 50 distinct sequences. If 40 of these occurrences are in a single taxonomic cluster, which contains 50 members and the remaining 10 occurrences are scattered among the remaining sequences the resulting value of $Q_s$ is 0.64. Finally, the user of the invention needs to understand that when members of a sequence cluster share an oligonucleotide which is not found in non-members of the cluster (e.g. when $Q_s$ is high) the oligonucleotide in question will almost always be found to occur in the equivalent place in all the 16S rRNAs that have it. This reflects the fact that useful signature sequences are phylogenetically conserved at various levels of genetic relationship. This is not obvious because it initially seems very counterintuitive. It is, however, the reason high quality signature oligonucleotides exist. If this were not the case the various oligonucleotides would be randomly scattered throughout the various sequences and high values of $Q_s$ would be uncommon and not predictive of what would be found in sequences that were not yet known.

It is also important to realize that there are many alternative ways in which the signature quality function, $Q_s$, is defined. One for example might take the logarithm of values or use values of $1-Q_s$. More to the point one could square the first factor in Equation 1 to give more weight on any false negatives or cube the second factor to strongly penalize false positives.

What size of oligonucleotides will give useful signature information? In the case of shorter small sequences, the equivalence of position is overshadowed for small oligonucleotides such as the 4,096 ($4^6$) different hexamers, many of which can be expected to occur by random chance among the 1,500 hexamers that one expects to find in a single 16S rRNA sequence. Thus, the heptamers ($4^7 = 16,384$ in total) represent the smallest sequence length that is likely to produce meaningful signature information. On the opposite side, large oligonucleotides tend to be unique to individual organisms. That is to say, as oligonucleotide size increases, a larger portion of the signatures will be for leaf nodes, e.g. small numbers of closely related organisms and a decreasing percentage will signify internal nodes. Based on prior experience with 16S rRNA ribonuclease T1 oligonucleotides, it is likely that sequences larger than length 15 will mainly have utility for leaf nodes.

Design and Implementations

Programming Language

Except the first program readseq, which is preinstalled as a binary executable, all other programs developed for this project were written in Perl.

Perl is a freely available, non-proprietary, open-source programming language. Thus, programs written in Perl will not be affected by possible future changes in the license of the language compiler/interpreter. Perl is also a very high-level language for general purposes. It has 4 function points per 100 lines of code, compared with 0.8 for C and 2 for C++. This means that software development in Perl is generally much faster than that in most other programming languages. Perl is especially efficient in dealing with text, which makes it an appropriate choice for manipulating genetic sequences. In addition, Perl's excellent built-in data structures, automatic garbage collection, and almost unrivalled portability also make it more attractive.

More information on Perl and its newest release can be found at the Perl web site: http://www.perl.com.2.2 Data structures.

All Perl built-in data structures, namely scalar, array, and hash, are used in this invention. Because of the complexity of the data presentations, more sophisticated data structures such as bi-directional binary tree and composite hash, are also used.

Given the characteristic structure of the phylogenetic tree, it was natural to represent it as a binary tree in the program. In this case the tree structure is special in that it is bi-directional. The parent tree node has a pointer to each of its two child tree nodes and the child tree node also has a pointer back to its parent tree node (FIG. 1). This unusual tree structure is required to facilitate the signature quality index value calculation at each branch tree node (excluding the tree root an all the leaf nodes).

Each leaf tree node has five data fields: "shortName", "fullName", "leafNumber", "isValid", and "isMatched" (FIG. 1). The first two fields hold the abbreviated name and the full name of the prokaryote. leafNumber records the sequentially assigned number of the leaf node in the tree. The last two are Boolean variables used mainly for calculation purposes. Each branch tree node has four data fields: "nodeNumber", "numLeaves", "numValidLeaves", and "numMatchedLeaves" (FIG. 1). The first field records the sequentially assigned number of the branch tree node. The other fields record the number of leaves, "valid" leaves, and "matched" leaves descended from this branch tree node respectively.

FIG. 1 shows the bi-directional binary tree structure with three leaf nodes. Note that a parent node has two pointers to its child nodes and each child node has a pointer back to its parent.

A composite hash was used to store all the oligonucleotides of a specific length derived from a dataset of the prokaryotic 16S rRNA sequences and their related information. The "infrastructure" of this composite hash was implemented with Perl's built-in hash. Because of the complexity of the information on each oligonucleotide, an anonymous hash data structure was heavily used to accomplish the task.

In Perl, a hash is composed of the unique keys and their corresponding values. The keys of the outmost layer of the composite hash are the sequences of the oligonucleotides and the value of each key is an anonymous hash which has three keys—"matchingTimes", "matchingOrg", and "treeNodeValues". The value of "matchingTimes" counts how many times the oligonucleotide occurs in the 16S rRNA sequence dataset. The value of "matchedOrg" is the set of the names the organisms whose 16S rRNA sequences are matched by this oligonucleotide. Because of the special nature of the hash—that is, its keys must be unique—the set is also implemented with an anonymous hash, whose keys are the names of the matched organisms and the corresponding values are set to "undef". The value of "treeNodeValues" records the five highest quality index values at the branch nodes. This is implemented with an anonymous hash whose keys are the branch tree node numbers and the corresponding values are the quality index values (FIG. 2).

FIG. 2 shows the elaborate structure of the composite hash used in the program. Only two entries are shown in this figure. A hash is represented by a table and the keys are shaded. ø denotes the data type "undef" in Perl. The data in this hash are for elucidatory purposes only.

Algorithm:

The signature quality index measures how well an oligonucleotide (probe) signifies a taxonomic group of prokaryotic organisms in the phylogenetic tree. Thus, the index qualitatively measures the "quality" of the signature sequences and ranges from 0 (no meaningful signature) to 1 (perfect signature). The index can be mathematically expressed as:

$$Q_s = (^I f_s) \times (1 - ^O f_s) \tag{1}$$

where $Q_s$ is a measure of signature quality, $^I f_s$ is the frequency of the signature sequence within the group under consideration, and $^O f_s$ is the frequency of the signature sequence outside the group of interest.

Given a defined group of prokaryotes, $^I f_s$ and $^O f_s$ can be empirically described as:

$$^I f_s = N_{GM}/N_{GT} \tag{2}$$

$$^O f_s = (N_M - N_{GM})/N_M \tag{3}$$

where $N_M$ is the number of probe-matched prokaryotes in the entire tree, $N_{GM}$ is the number of probe-matched prokaryotes in the group of interest, and $N_{GT}$ is the number of prokaryotes in the group under consideration. Interpolate equation (1) with equations (2) and (3), we have:

$$Q_s = (N_{GM}/N_{GT}) \times (1 - (N_M - N_{GM})/NM) \tag{4}$$
$$= (N_{GM}^2)/(N_{GT} \times N_M)$$

Preferably, the invention uses equation (4) to calculate the signature quality index $Q_s$ and in order to do so during run time it keeps tracking $N_{GM}$, $N_{GT}$, and $N_M$ of every oligonucleotide of a specific length at every internal tree node. Since equation (4) is derived from equations (1), (2), and (3), if any one of these three equations changes, which may occur based on new insight into how characteristic signatures occur and are distributed in 16S rRNA sequences, equation (4) will change accordingly. This great flexibility provides system improvements that are included in the invention.

System Implementation

The identification system used to find characteristic oligonucleotides in the 16S rRNA sequence dataset consists of the following twelve principal programs and several auxiliary programs, all provided on the CD enclosed with the application.

Figure 3:
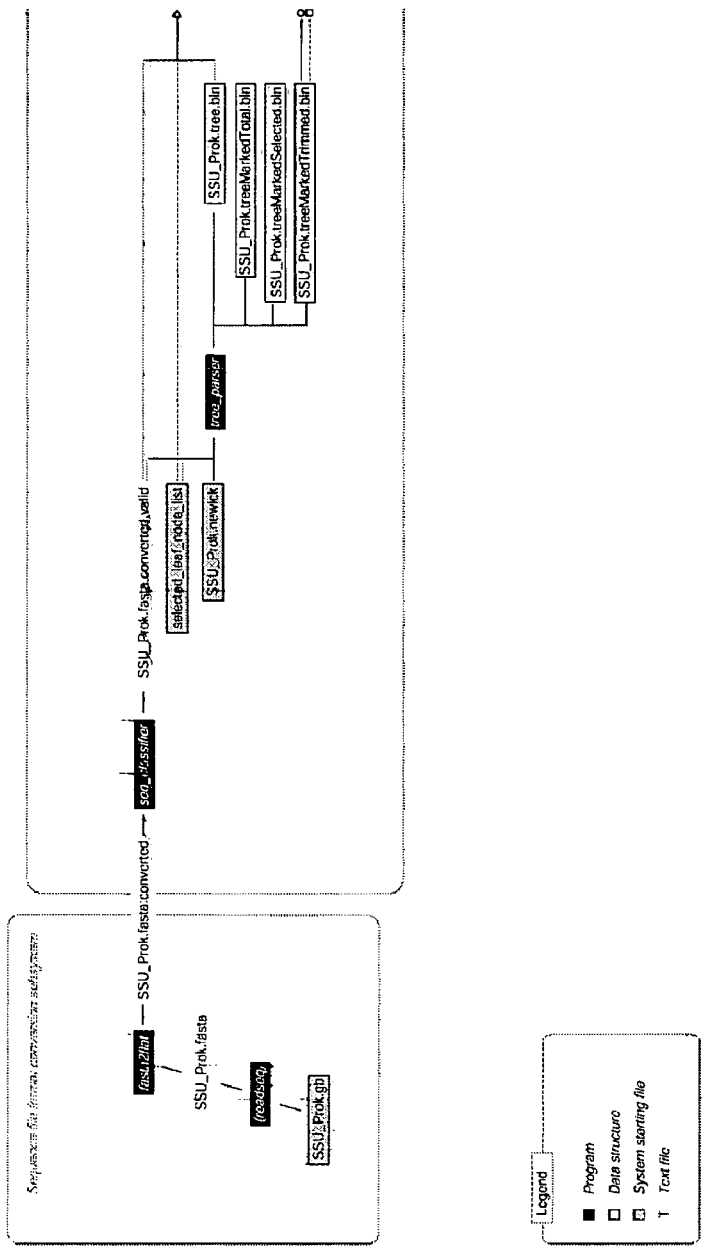
FIG. 3 shows schematically the flow chart of the principal programs.
Figure 3:
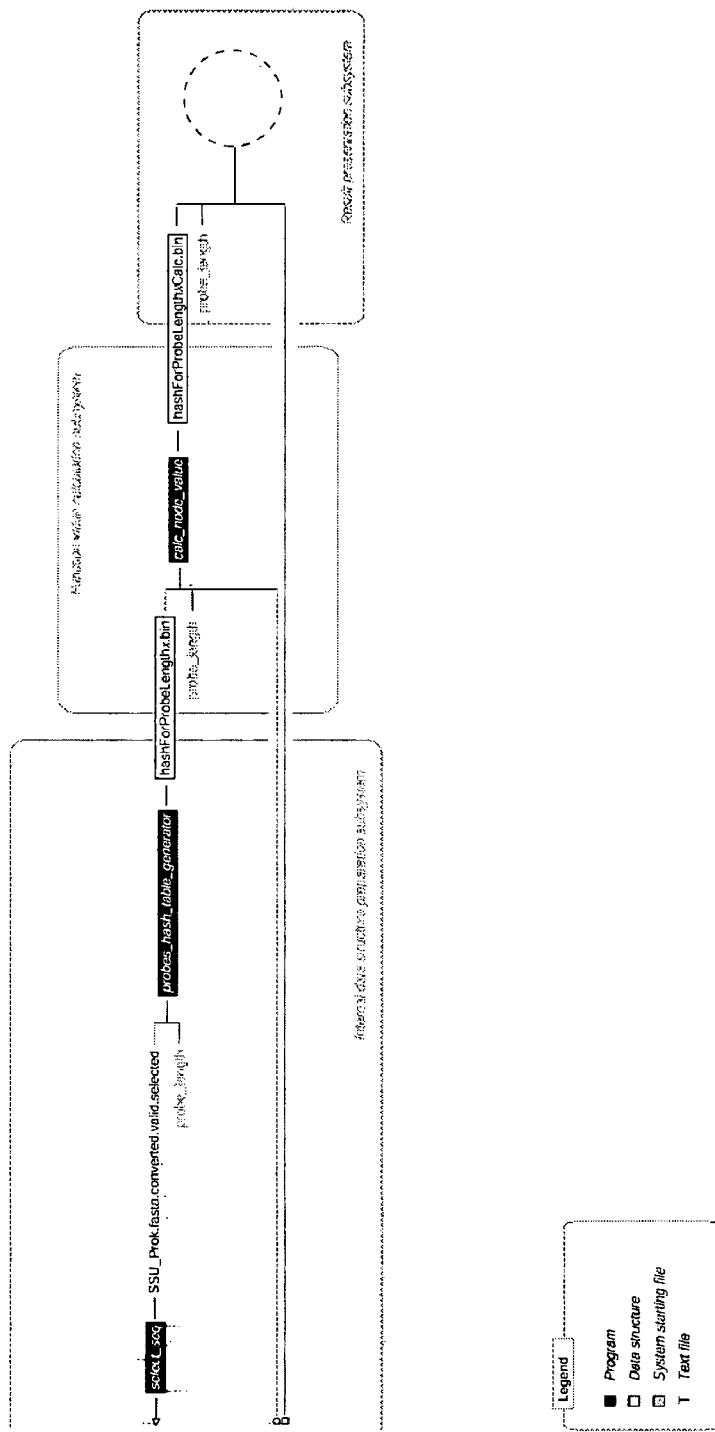

Principal programs:
readseq (preinstalled program, not written by the author)
fasta2flat
seq_classifier
tree_parser select_seq
probe_hash_table_generator
calc_node_value
result_printer & result_printer_
group_node_lister
list_hit_branch_nodes
hybridize
Auxiliary programs:
node_selector
tree2newick FIG. 3 gives a panoramic view of the relationship among the principal programs and the data flow in this system. This oligonucleotide identification system can be roughly divided into four functionally different subsystems, which in turn carry out sequence file format conversion, internal data structure preparation, function value calculation, and result presentation respectively (Table A).

The unaligned prokaryotic 16S rRNA sequences were downloaded from the RDP in Genbank format. The 16S rRNA sequences are from those prokaryotic organisms that appear in the comprehensive prokaryotic phylogenetic tree. Genbank format is the standard format for annotated nucleic acid and protein sequences. In this format, a sequence is recorded with several fields of information including its locus, definition, reference, and origin. Since only the abbreviated names of the organisms and the 16S rRNA sequences in the sequence file are needed for the purpose of this project and all other information is redundant, it is necessary to extract the needed data from the sequence file and discard the extra in order to increase the program efficiency.

This data extraction functionality is fulfilled by subsystem I, the sequence file format conversion subsystem, which is composed of readseq and fasta2flat (FIG. 4). Readseq is a preinstalled program. It is a convenient and useful utility to convert the format of a sequence file among Genbank, FASTA, and many other formats. FASTA format is also a common sequence format and usually used in sequence alignment. In this format, a right angle bracket (">") prompts the sequence annotation on the same line, which is followed by the sequence itself starting on a new line. This project used readseq to change the 16S rRNA sequence file from Genbank format to FASTA format. In this step only the names of the organisms and the 16S rRNA sequences are retained while all other information is discarded.

Since the 16S rRNA sequence is long and expends several lines in FASTA format, if is not convenient to use the sequences in this format. To further facilitate the manipulation of the 16S rRNA sequences and the corresponding organism names, the program fasta2flat takes the sequence file in FASTA format as the input and rewrites the sequence data in a "flat" format, in which every line is a data entry starting with the organism name, followed by a tab character ("\t") as the separator followed by a string of letters (A, U, G, C), which is the 16S rRNA sequence.

As shown in FIG. 4, Subsystem I converts the format of the sequence file. Subsystem II builds the binary prokaryotic phylogenetic tree and the composite oligonucleotide hash. These internal data structures were used to calculate the function value at each branch tree node.

Release 7 from RDP contains a total of 7,322 prokaryotic 16S rRNA sequences. However, not all of these sequences can be used to generate the set of oligonucleotides (please refer to the section on program probes_hash_table_generator for explanation on how the set of oligonucleotides was generated), because many of them are only partial sequences of 16S rRNAs (e.g. a sequence has only 300 nt instead of about 1,500 nt, the full length of 16S rRNA) and many contain positions in the sequences that have not been fully determined (i.e. if any position is noted by a letter other than A, U, G, and C). Program select_seq filtered out these problematic "invalid" sequences and retained 1,921 "valid" sequences that are fully determined and longer than 1,400 nt.

The comprehensive prokaryotic phylogenetic tree based upon 16S rRNA sequence in Newick format was obtained from the RDP web site. The Newick format for representing trees in computer-readable form makes use of the correspondence between trees and nested parentheses, noticed in 1857 by the famous English mathematician Arthur Cayley. A simple exemplary tree and its corresponding Newick format are depicted in FIG. 5.

Figure 5:
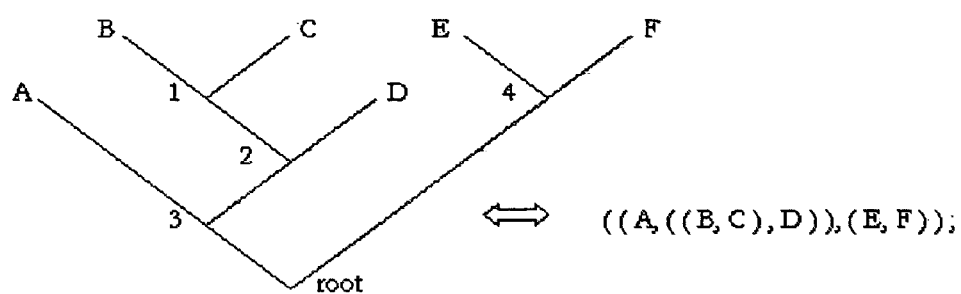
FIG. 5 shows schematically a phylogenetic tree and its corresponding Newick format presentation.

As shown in FIG. 5, the invention can form a phylogenetic tree and its corresponding Newick format presentation.

Figure 7:
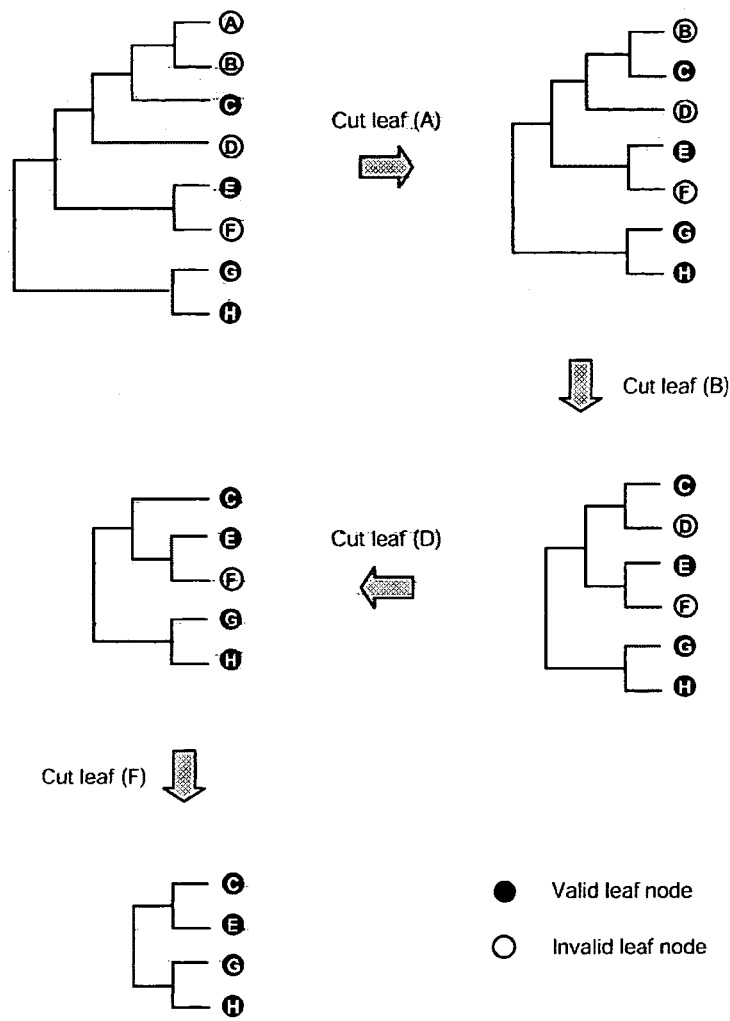
FIG. 7 shows schematically the trimming is stepwise and topology-conserving

The tree in Newick format ends with a semicolon. Interior (branch) nodes are represented by a pair of matched parentheses. Between them are representations of the nodes that are immediately descended from that node, separated by commas. The tree in FIG. 7 has six leaf nodes at the tips (A, B, C, D, E, and F) and five branch nodes inside (the root node and the branch nodes 1-4). A branch node can be at any place where a leaf node locates, which results in further nesting of parentheses to any level. The comprehensive prokaryotic phylogenetic tree has 7,322 leaf nodes and 7,321 branch nodes. Since the tree is far from being balanced (as the evolution of life itself is not balanced), some branches of the tree go very deep.

The Newick format of the tree file obtained from the RDP website largely conforms to the Newick Standard described above with minor differences, such as the usage of comma and single quote. See FIG. 10 for an example. The tree file contains taxonomic group identifiers and branch lengths. Much information is also recorded for every leaf node, which includes the abbreviated organism name, the full name, and etc. When the program tree_parser parses the tree file and builds the internal tree structure, only the abbreviated and full names of the organism are kept for each leaf node and all other information is discarded. The abbreviated name is later compared with every name in the set of matched organisms of every oligonucleotide to determine if this leaf node is matched by a particular oligonucleotide. The full name is used purely for illustrative purposes whenever clear identification of an organism is necessary. Since this system does not use taxonomic group identifiers and evolutionary distances, these data in the tree file were also ignored.

Figure 6:
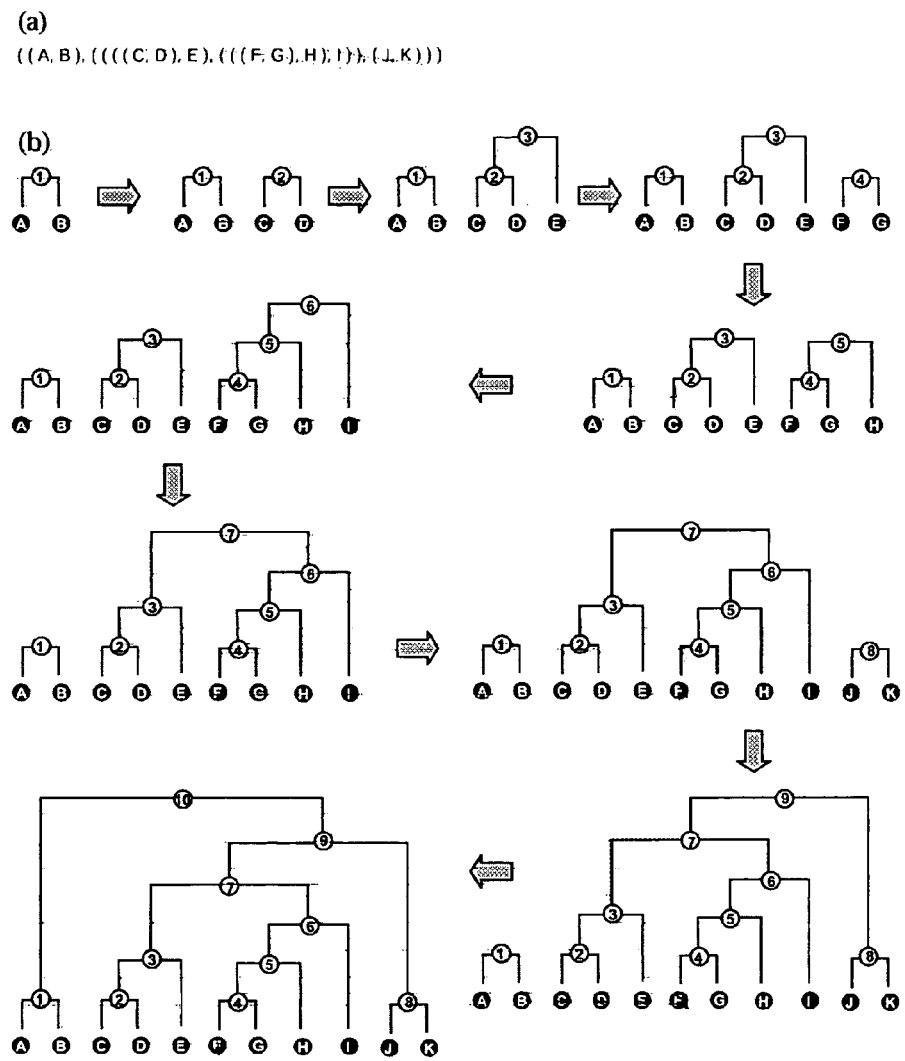
FIG. 6 shows schematically the tree file in Newick format is parsed in a stepwise and bottom-up manner

Due to the algorithms and methods used to construct the phylogenetic tree, almost all hylogenetic trees are bifurcating, that is, a branch node has exactly two child nodes: a left node and a right node. This feature of a phylogenetic tree makes a binary tree a natural and excellent choice of data structure to present it in a program. In some cases, the distinction between the relative branching orders is very close and three or more branches are shown as emerging at the same node. Such nearly bifurcating trees are not a problem for the method as they are readily reduced to a bifurcating tree. The tree file in Newick format is parsed in a stepwise and bottom-up manner. Program tree_parser scans the tree file and add one leaf node a time to the nascent internal tree facilitated by a stack of references. FIG. 6 shows how a simple internal binary tree is built step by step (the reference stack is not shown).

FIG. 6 shows how the tree file in Newick format is parsed in a stepwise and bottom-up manner. (a) A phylogenetic tree in Newick format. (b) The internal tree structure is built stepwise and from the bottom up. The filled circles denote leaf nodes and the hollow circles branch nodes.

Program tree_parser builds the internal comprehensive prokaryotic phylogenetic tree using the tree file in Newick format as the blueprint and serializes it to an external binary file SSU_Prok.tree.bin for possible later use. It then marks the leaf nodes in the internal tree structure "valid" or "invalid" according to the names of prokaryotes in file SSU_Prok.fasta.converted.valid, the output of program seq_classifier, and serializes the marked tree to file SSU_Prok.treeMarkedTotal.bin. This tree structure can be used later to calculate the function values, but the process is inefficient because nearly 74% of the leaf node sequences are not of the very highest quality. The tree is large and the existence of invalid leaf nodes makes its size unjustifiable. Another difficulty is that some taxonomically different branch nodes may actually represent the same group of valid descendant leaf nodes.

These potential difficulties were avoided by using a representative tree based on only the highest quality sequences. Building such a representative tree requires a comprehensive analysis of the existing published tree of 7,322 sequences to determine which groupings and individual sequences, e.g. known pathogens, need to be included. This representative tree met these three qualifications:

It only contains bacteria whose 16S rRNAs have been fully sequenced.

At least one organism represents each major taxonomic grouping.

The topology of this representative tree should conform to that of the comprehensive tree. In order to construct a representative tree, 929 bacteria are selected from 1,921 prokaryotes whose 16S rRNA sequences are of the highest quality. The list of the leaf node numbers of these 929 prokaryotes was kept in the text file selected_leaf_node_list. The resulting representative tree is far more comprehensive than the 98-sequence version provided RDP with its Release 7 dataset.

In order to keep the topology of the representative tree in accordance with that of the comprehensive tree, after writing out the binary files SSU_Prok.tree.bin and SSU_Prok.treeMarkedTotal.Bin, program tree_parser used the list of selected leaf nodes in file selected_leaf_node_list as the reference to "trim away" (FIG. 7) invalid and valid-but-unselected leaf nodes in the tree structure, resulting in a representative tree with 929 valid leaf nodes. This trimmed tree structure was serialized to the binary file SSU_Prok.treeMarkedTrimmed.bin, which was later used in the signature quality index value calculations.

FIG. 5 illustrates that the trimming is stepwise and topology conserving. Program select_seq takes three files SSU_Prok.fasta.converted.valid, selected_leaf_node_list, and SSU_Prok.tree.bin as the input and generates file SSU_Prok.fasta.converted.valid selected as the output, which will be used to construct the composite oligonucleotide hash in the next step. Input file SSU_Prok.fasta.converted.valid is the output of program seq_classifier. It contains all "valid" 16S rRNA sequences in a special "flat" format. File selected_leaf_node_list keeps all leaf node numbers of the selected prokaryotes. SSU_Prok.tree.bin is the binary file from which the comprehensive prokaryotic phylogenetic tree is retrieved. The tree structure is used to index between the leaf node number and the abbreviated organism name in the corresponding leaf node. The output file holds the 16S rRNA sequences of the selected organisms in the same format as SSU_Prok.fasta.converted.valid.

Program probes_hash_table_generator is responsible for generating the composite hash, which records the needed information for each of all occurring oligonucleotides of a specific length from the 16S rRNA sequences dataset. The program takes the probe length (x) as the command line argument and implicitly open sequence file SSU_Prok.fasta.converted.valid selected to get the abbreviated names of selected organisms and their corresponding 16S rRNA sequences. The hash for probes of length x is output as binary file hashForProbeLengthx.bin.

Since only the oligonucleotides occurring in the 16S rRNA sequences are considered interesting, naturally all oligonucleotides and their initial cognate information used in this system are derived directly from the 16S rRNA sequences. If we consider the number of all possible oligonucleotides of a specific length, the computational saving by deriving oligonucleotides directly from 16S rRNA sequences is substantial. Out of all possible 1,048,570 ($4^{10}$) decamers, 236,884 of them actually occur in the dataset of the 1,921 "valid" 16S rRNA sequences and 133,599 of them occur more than once. Only these 133,599 multi-occurring decamers (12.7% of all) are used in the next step to calculate the function values since we are only interested in identifying the phylogenetic neighborhood/group of an unknown bacterium. By definition oligonucleotides that are unique cannot be characteristic of a group.

Figure 8:
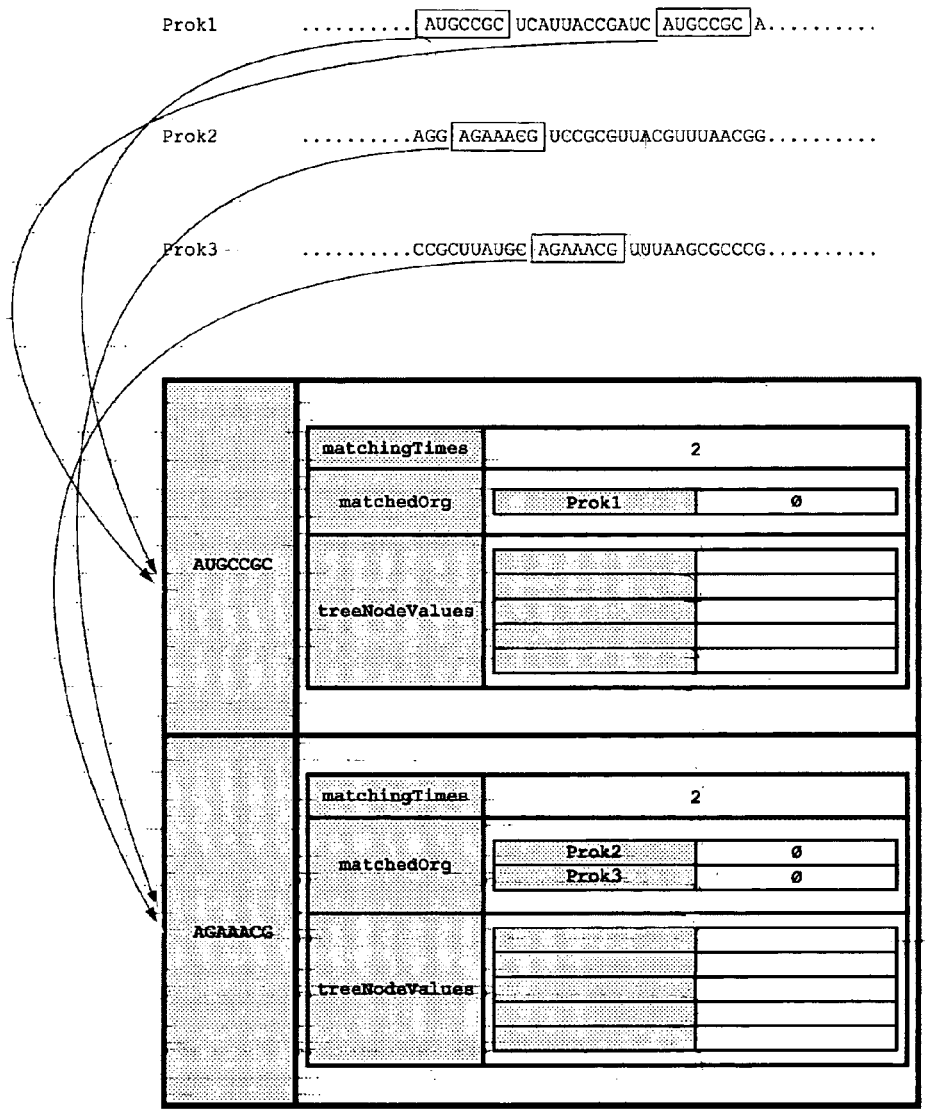
FIG. 8 shows schematically the composite hash of the oligonucleotides is built from the 16S rRNA sequences

Program probes_hash_table_generator reads in the selected 16S rRNA sequences and for each sequence it excises oligonucleotides of the specified length from the 5' end, shifting one nucleotide at a time, to the 3' end (FIG. 8). Since an oligonucleotide can occur in 16S rRNAs from several organisms and several times in one particular 16S rRNA, the occurring times (matchingTimes) of an oligonucleotide in the hash can only be equal to or greater than the number of the organisms (matchedOrg) whose 16S rRNAs it occurs in. FIG. 8 illustrates how the composite hash of the oligonucleotides is built from the 16S rRNA sequences.

At this point the system has completed the necessary preparative work, namely the sequence file format conversions and the data structure constructions. With those steps complete, the system is now ready to calculate the function value at each branch tree node. Subsystem III, the function value calculation subsystem, consists of only one program—calc_node_value. It takes the probe length (x) as the command line argument and implicitly reads in the corresponding binary probe hash file hashForProbeLengthx.bin and the binary tree file SSU_Prok.treeMarkedTrimmed.bin.

For each multi-occurring oligonucleotide from the hash reconstructed from the binary hash file, leaf nodes in the phylogenetic tree are marked if this sequence occurs in the 16S rRNAs of the organisms at these leaf nodes. At each branch node the number of its descendent marked leaf nodes is counted by using the unusual backward pointers in the tree structure. The signature quality index values are calculated at all the branch nodes and then sorted in descending order. The top five highest values and their corresponding branch node numbers are kept as the value/key pairs in the treeNodeValues anonymous hash field of this probe in the composite hash. After the calculation is completed the result is output as a binary file hashForProbeLengthxCalc.bin, which is essentially the same as the hashForProbeLengthx.bin except that the treeNodeValues for each multi-occurring oligonucleotide is populated with the calculation results.

Subsystem IV, the result presentation subsystem, reconstructs the composite probe hash and retrieves the calculation results from file hashForProbeLengthxCalc.bin. It is the open end of the system: the calculation result can be analyzed and presented in a variety of ways because any program, as long as it can reconstruct the composite hash from the binary file, can "plug into" the system via the subsystem IV and interpret the calculation results in its own way. Currently this subsystem consists of five programs (Table C).

Programs result_reporter and result_reporter_, as their names suggest, are a pair of similar result-presenting programs. They both take the length of probe (x) as the command line argument, reconstruct the composite hash filled with the calculation results from corresponding hashForProbe-Lengthx Calc.bin, and give a list of signature sequences with information on their quality index, their identified branch nodes, and the descendent leaf nodes as the output files. The only difference between these two programs is that the former outputs the list of signature sequences sorted in descending order of the node numbers of the identified branch nodes while the list output by the later is sorted in descending order of the signature quality indexes.

Programs group_node_lister and list_hit_branch_nodes present the result from the perspective of the taxonomic groups. group_node_lister lists all identified branch nodes along with their corresponding signature sequences of a particular length specified at the command line. list_hit_branch_nodes takes a more ambitious approach. It gets all the calculation results of oligonucleotides from heptamer to undecamer from files hashForProbeLengthxCalc.bin (x=7~11) and collects the number of times that a branch node is identified by characteristic oligonucleotides of a specific length at signature quality levels 0.6, 0.8, and 1.0 respectively. The analysis result of this program is the useful statistics which imply the relationships among the frequency with which a branch node is identified, the oligonucleotide length, and the signature quality.

Program hybridize was used to test the usefulness of the characteristic oligonucleotides that the system has discovered so far. It takes a sequence file as the input in which every entry starts with a label followed by a tab character ("\t") as the separator followed by the actual 16S rRNA sequence. Although this program can use any reasonably good set of characteristic oligonucleotides as the hybridization probes, in this preliminary test nonameric signatures were used and they gave satisfactory results. When hybridize reads in a 16S rRNA sequence, it compares ("hybridizes") this sequence against all the characteristic oligonucleotides with a signature quality better than a specified threshold in the selected probe catalogue. When a probe is expected to bind to the 16S rRNA it is recorded by marking the corresponding branch node in the representative phylogenetic tree. The output of hybridize is one marked representative tree per each unknown 16S rRNA sequence plus a signature quality threshold (0.6, 0.8, or 1.0). Some interesting and noteworthy features of the results will be discussed later.

Valid 16S rRNA Sequences

The 7,322 bacterial 16S rRNA sequences obtained from RDP release 7 have multifarious qualities. Some were fully determined in terms of both the length and every position of the sequence while others are either partially sequenced and/or contain one or more undetermined positions. Any sequence that was either less than 1,400 nucleotides in length or has nucleotides other than AUGC (e.g. especially N standing for a position where the sequence could not be determined) was considered "invalid" by the system and was filtered away. Many of these sequences had very minor difficulties, i.e. marginally shorter than required or containing up to 3 uncertain sequence assignments and could have been used without significant effect. However, since 1,921 16S rRNA sequences met the strongest criteria it was possible to maintain the very highest standard. Thus only the sequences deemed valid were retained to generate the sets of signature oligonucleotides.

Although the two conditions disqualifying problematic 16S rRNA sequences greatly simplify how the system deals with low-quality sequences, they are probably far too strict and as a result the current calculations likely did not make maximum use of all the sequence information in the dataset. Sequences a few nucleotides short of 1,400 nt or those that contain a small number of undetermined positions are currently discarded, even though their signature sequences remain mostly intact. To mitigate this problem, the quality demands can be moderately relaxed, i.e. by lowering the length requirement and only discarding the oligonucleotides containing undetermined positions instead of the whole 16S rRNA sequence. However, if a representative phylogenetic tree is used instead of a comprehensive one (as in this system), the effect of losing sequence data should be mild since only a subset of 16S rRNA sequences are used anyway. If a branch of the comprehensive phylogenetic tree is absent from the representative tree due to lack of valid 16S rRNA sequences in that cluster, either the quality demands can be decreased as described above or sequences from two very closely related organisms can be fused to ensure that this particular branch will be included. Also, it should be appreciated that in some cases, the distinction between the relative branching orders may be very close in some areas of the tree. When this occurs it is not uncommon to show three or more branches emerging from the same node. Such nearly bifurcating trees are not a problem for the method as they are readily reduced to a bifurcating tree.

Oligonucleotides in 16S rRNA Sequence Dataset

Figure 9:
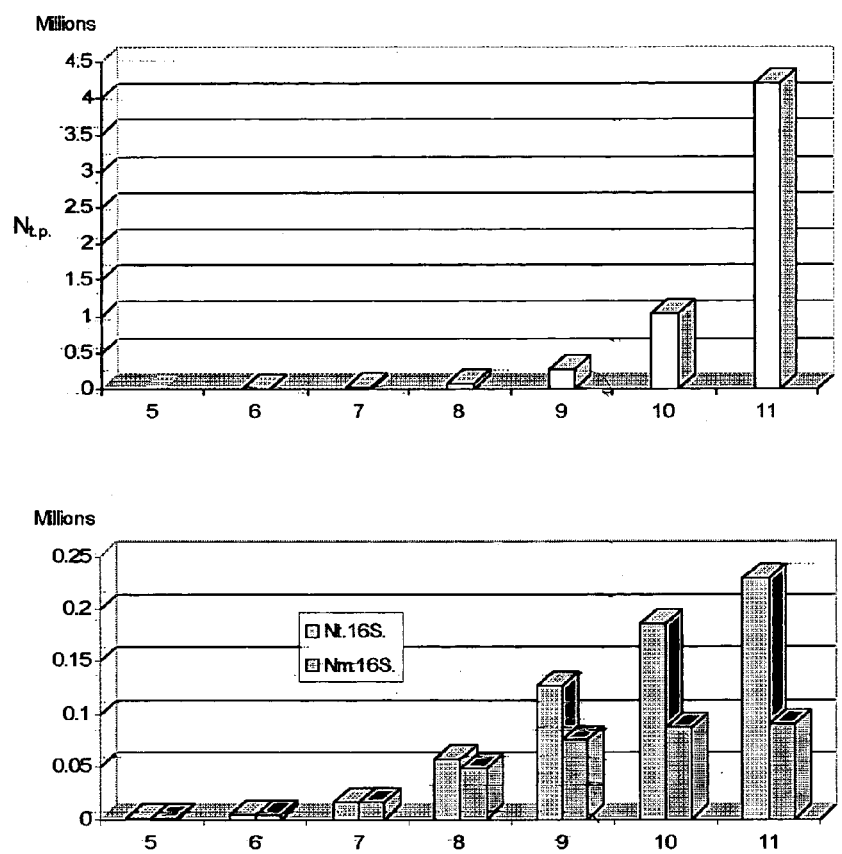
FIG. 9 shows schematically how the number of oligonucleotides and their respective lengths length are related.
Figure 11:
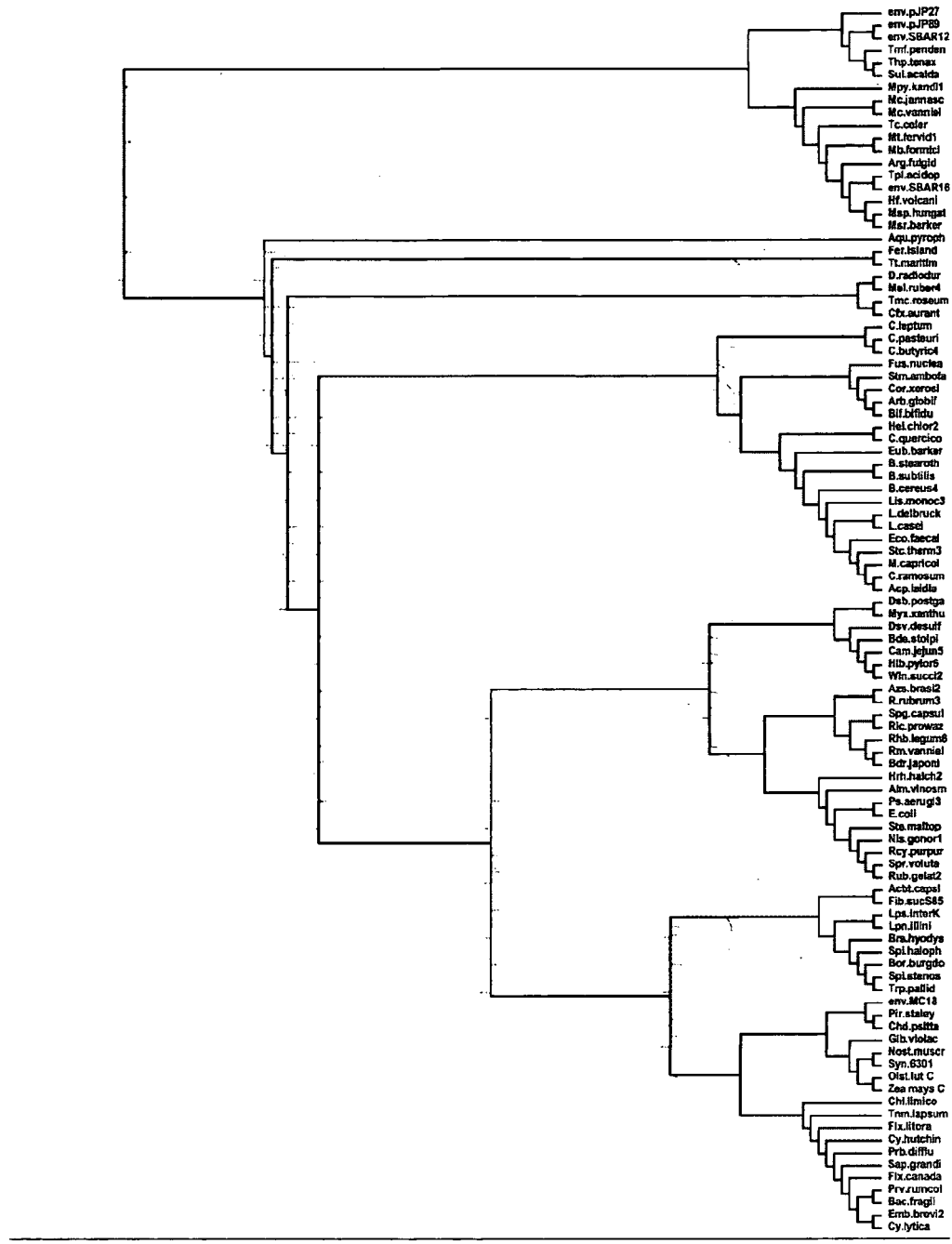
FIG. 11 shows a graphic view of the representative prokaryotic phylogenetic tree.

The number of all possible oligonucliotides of a specific length evidently depends on both the length and how many different nucleotides are legitimate at each position. Given that there are four different nucleotides (A, U, G, C in RNA and A, T, G, C in DNA), if the length of the oligonucleotide is n, the number of all possible length-n oligonucleotides is $4^n$. When length n is large, the oligonucleotides occurring in the 16S rRNA sequence dataset are only a non-random fraction of all possible oligonucleotides and there is no simple formula to calculate this number. Table D summarizes these numbers for oligonucleotides under consideration in this system from hexamer to undecamer. FIG. 9 plots these data and gives a direct visual perception of the trends.

FIG. 9 shows that the number of oligonucleotides and the length are related. (a) The number of all possible oligonucleotides increases exponentially with the length. The curve is described by function $f(x)=4^n$. (b) The numbers of the total and multi-occurring oligonucleotides in the 16S rRNA sequence dataset also increase with the length. The increases are slower than that in (a) due to the sequence context constraint from 16S rRNA.

Signature Oligonucleotides in 16S rRNA Sequence Dataset

At a branch node in the phylogenetic tree, if an oligonucleotide gives a quality index value greater than a preset value, this oligonucleotide is said to be a signature at that branch node since it can identify that node better than other oligonucleotides which have a lower value of the quality index. In the current system, 0.6 is the cutoff value, i.e. only oligomers with function value over 0.6 at a branch node will be presented in the results.

Of course, several signatures may identify a branch node and an oligonucleotide may also be a signature simultaneously at several branch nodes. Clearly, the higher the quality index value of a signature at a branch node is, the better it can identify that node. A signature with a function value of 0.8 is better than one with a function value of 0.6 at the same branch node and a signature with function value 1.0 is perfect for that node, which, according to the definition of the signature quality function, $Q_s$, means that all 16S rRNAs having this signature sequence are in the same phylogenetic group defined by that branch node and thus no 16S rRNAs with the same signature are outside that group.

Signatures of different lengths are distributed in the phylogenetic tree differently. The general observation is that long and short signatures have polar distributions in the tree: the long signatures tend to identify the branch nodes near the tree leaves while the short ones are more likely to pick out those near the tree root. This trend is evident when the results of pentameric and undecameric signatures are compared. The result shows that 35 out of 35 (100%) perfect ($Q_s=1.0$) pentameric signatures identify the root while 11,958 out of 18,746 (64%) perfect undecameric signatures identify the two-leaves as two children branches.

Short signatures, e.g. pentamers and hexamers examined by the system, are generally too unspecific to identify any interesting small groups in the phylogenetic tree with $Q_s$. They tend to identify the whole bacterial tree instead. However, if a smaller nucleic acid such as 5S rRNA is used then sequences of this length might be significant. On the other hand, long signatures, e.g. undecameric and longer oligonucleotides, are increasingly specific and therefore more useful to identify individual organisms and two-leaves-as-two-children groups. Signatures with a length between seven and eleven should have a more balanced distribution in the phylogenetic tree.

2,533 nonameric signatures can identify phylogenetic groups with three or more (up to 23) members perfectly. On >0.8 and >0.6 quality levels there are 5,580 and 15,340 nonameric signatures respectively. At this length, the signature sequences cover/identify ~80% of the phylogenetic groups in the representative tree. The user can refer to Table E for a quick comparison.

In Table E a "gap" between the numbers of signatures shorter than octamers and those longer than heptamers is evident. On every level of signature qualities examined, namely where $Q_s$ is equal to 1.0, 0.8, or 0.6, there is a sharp unexpected increase in the number of signatures and tree coverage from heptamers to octamers.

Table E provides a comparison among signatures of various lengths ranging from pentamers to undecamers and also 15-mers. Only signature sequences that can identify phylogenetic groups with three or more members are counted in constructing this table. A computer program is used to calculate the coverage. Any branch nodes other than those that have two leaf nodes as their two child nodes in the representative tree are regarded as phylogenetic groups (635 in total). The signature quality $Q_s$ is greater than 0.6.

ILLUSTRATIVE EXAMPLES

Example 1

A Local Region of the Tree & its Associated Signatures

Figure 12:
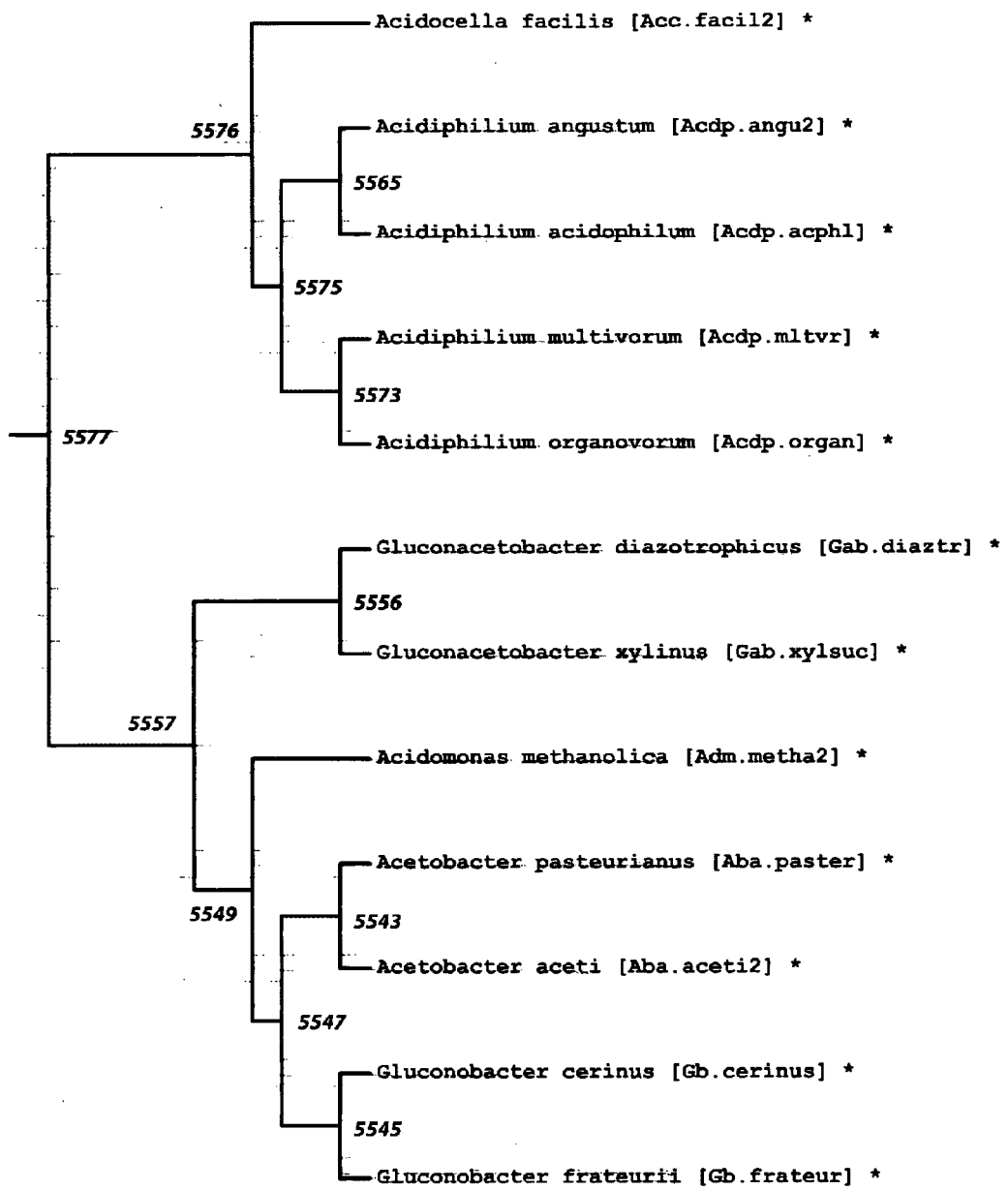
FIG. 12 A local region of the representative tree following trimming from 38 to 12 sequences. The branch numbers in the representative tree are labeled in the picture and can be correlated with the results given in Table F. The complete representative tree is given in Newick format in FIG. 10 and shown in graphical form on the CD that is part of this application Table A illustrates by example certain information, which is on the CD that is part of this application. The table illustrates for test sequences of length 15 the five best signature quality scores and the nodes they are associated with in the phylogenetic tree.

The purpose of this example is to better illustrate the relationship between the signature sequences found and the nodes of the tree used in a more detailed level. Table F, lists only the results with reference to a local region of the comprehensive tree. Before trimming this region contained 16S rRNAs representing 38 organisms. A total of 23 of these sequences were of the very highest quality but many of them were very similar so a total of 12 sequences were selected for final inclusion in the representative tree. This local region of the representative tree is shown in FIG. 12. The numbers of nonameric, undecameric and 15-mer signature sequences at each of the 11 branch tree nodes in this 12 organism sub-tree in different ranges of quality levels are summarized in Table F. Tree node 5547 does not have any signatures at the Qs 1.0 level whereas its parent branch, node 5549, has 14 perfect nonameric/undecameric/15-mer signatures. Several of these are the same sequences, which serve as signatures for node 5547 at values of Qs at the 0.8 level. This result draws attention to the fact that many individual oligonucleotides are signatures of several branch nodes at differing levels of $Q_s$. This reflects the child/parent relationship between nodes. The signatures identifying the taxonomical group represented by the local root node 5577 of the representative tree illustrate another common feature. Of the 17 perfect signatures for node 5577, five are nonameric, six undecameric and six are 15-mers. However, every one of these five nonameric signatures appears as a part of one of the six undecameric signatures. This inclusion of shorter signature sequences is a part of a longer one is frequently seen regardless of the signature length, the signature quality level and the position of interest in the phylogenetic tree.

Example 2

In Silico Hybridization

Once the characteristic oligonucleotides (signature sequences) from 16S rRNA sequence dataset are identified, they can be used to implement in silico hybridization (This is not carried out in the laboratory. Instead, it is performed virtually by a computer program, thus, in silico). This procedure can be either executed as a standard experimental routine or in this case as a quick test of the validity of the signatures, which have been identified.

Since these characteristic oligonucleotides were derived from the selected valid 16S rRNA sequences using the corresponding representative tree, several valid 16S rRNAs that were not selected to make the representative tree were chosen as 16S rRNAs from "unidentified" bacteria. Program hybridize was used to perform in silico hybridization between the unknown 16S rRNAs and the characteristic oligonucleotides. The unknowns were thus placed in their predicted phylogenetic neighborhoods in the representative tree. Because the comprehensive phylogenetic tree is available, thus the validity of the predictions could be quickly and definitively checked.

This in silico hybridization experiment was set up with these the following parameters: Probes length: 9 (nonameric) and 11 (undecameric) quality level: 0.6, 0.8, and 1.0
16S rRNAs control: *Escherichia coli* (*E. coli*)
tests with the following valid sequences:
  *Methanobacterium formicicum* (Mb.formici)
  *Tetragenocuccus halophiles* (Tgc.halop2)
  *Orientia tsutsugamushi* (Ort.tsuts6)
test done with following invalid sequence:
  the isolate M2 of the symbiont of methanogen (sym.M2)
The four agents in this example are chosen in a random way with maximum distribution in the comprehensive tree.

The results of this example are very promising. All five bacteria, namely one control and four test organisms, are placed in the correct phylogenetic neighborhoods. The correctness of the placements is confirmed by the positions of those five organisms in the comprehensive tree.

The control, *E. coli* at leaf node 7270 under branch node 7224 in the comprehensive tree, is unambiguously placed under branch node 7259 with *E. coli* (itself), *E.coli*7, and

*E.coli*rnG3 as three leaf nodes when probes at Qs 1.0 are used The best example of the four cases is probably Ort.tsuts6, which resides at leaf node 5404 under branch node 5383 in the comprehensive tree. This prokaryote was uniquely placed under branch node 5391 with Ort.tsuts9 at the only direct leaf node 5411 of this branch node. Another particularly noteworthy and interesting case is the identification of sym.M2. The sequence of the 16S rRNA from this organism has only 359 nucleotides with one undetermined position. The correct placement of this prokaryote in the representative tree was possible because some signature sequences in its poorly sequenced 16S rRNA apparently remained intact and identifiable.

Although the prokaryotic organisms could be placed in correct clusters, there were positive errors, i.e. some groups, which are not in the correct phylogenetic neighborhoods, were positively identified. This kind of error occurs because many of the signature sequences used have a value of $Q_s$ of less than 1. The number of these false positive errors decreased as the probe quality Qs increased from 0.6 to 1.0, but as to a specific organism and a specific probe quality level there was no dramatic difference in the error rate between using nonameric and undecameric probes. Despite this imperfection, one point should be stressed: even though the false positives occur, the correct phylogenetic neighborhoods are among the groups identified in all cases. Moreover, the correct neighborhood is readily identified by the presence of multiple hits whereas the noise placements are frequently loners. This is a very important aspect of the method, which stems directly from the parent/child relationship between nodes in a bifurcating tree. Thus, false positives are not a serious impediment to success. False negatives are also not a problem because of the redundancy of signature sequences that occur at many nodes.

This example shows that when a small set of 16S rRNA sequences are analyzed, at least some signature sequences exist that are representative of the phylogenetic groups that can be identified by tree constructions based on the complete 16S rRNA. sequences. The consequence of having thousands of such sequences in the dataset was not known in the prior art. Possibly noise would build Up to the extent that useful signatures would be obscured. Even if such sequences continued to exist in the larger data set it was not clear that their numbers would be useful nor was it clear that they could be, readily identified.

The results establish beyond any doubt that characteristic oligonucleotides in the bacterial 16S rRNA sequence dataset do in fact exist in huge numbers. Over 15,000 nonamers alone were identified, with in many cases multiple coverage of the various phylogenetic groupings in the 929 organism representative tree.

It is invaluable to identify these signature sequences because a group of evolutionarily related bacteria can be distinguished from other groups by a set of characteristic oligonucleotides specific to that group. The existence of these signatures is a direct demonstration of an innate characteristic of the evolution of bacterial 16S rRNAs that can be utilized to identify an unknown prokaryotic agent by elucidating its immediate phylogenetic neighborhood. These characteristic oligonucleotides can be used as the basis for developing hybridization probes that can be used in order design valuable oligonucleotide microarrays. Herein the utility of the signature sequences was tested by in silica hybridizations using as unknowns sequences that had not been included in the original representative tree. These studies demonstrated that the characteristic oligonucleotides in the unknown organisms readily provided their correct placement in the tree.

This example by no means limits the invention to characteristic oligonucleotides in 16S rRNA sequence dataset. On the contrary, it encompasses many variations and specific improvements including, but not limited to the following:

1. Use of new data available at RDP (both the newly released 16S rRNA sequences of release 8.1 and an updated prokaryotic phylogenetic trees).
2. Improvements to the representative tree, e.g. to provide that every cluster of prokaryotes in the comprehensive tree is represented by at least one bacterium in this tree. Where possible, merging of pairs of two closely related but not full length sequences to obtain a full length representation of that tree region may be possible. It also may be useful to better weight the number of entries from various clusters.
3. Use of different but sensible functions to calculate the signature quality index. Since the quality index is the most important tool for evaluating the signature potential of oligonucleotides in this system, changing the function can have a substantial impact on the specific result.
4. Assembling and use of a comprehensive set of characteristic oligonucleotides, by which the majority of the groups and all of the important groups in the representative tree can be identified. The oligonucleotides in this set are likely to have various lengths.
5. Applying mathematical and programming techniques to facilitate the final interpretation of hybridization results.

Example 3

Soil Samples 16S rRNA is purified from an unknown organism isolated from soil and amplified by RT-PCR using primers directed to conserved regions and flanking a variable region of the molecule. The PCR products are subjected to digestion by a restriction endonuclease, flourescently labeled with cy5, and then hybridized to an array of all possible 8-mer peptide nucleic acids. After washing, the pattern of hybridization is observed by confocal laser fluorescence scanning, and interpreted in terms of the known signature sequences for bacteria and the organism is assigned to the genus *Nocardia*.

Example 4

Soil Samples 16S rRNA is purified from an unknown organism isolated from soil and amplified by RT-PCR using primers directed to conserved regions and flanking a variable region of the molecule. The PCR products are subjected to digestion by a restriction endonuclease, fluorescently labeled with cy5, and then hybridized to an array of 5,000 DNA probes designed to recognize the 16S rRNA sequences of particular species. After washing, the pattern of hybridization is observed by confocal laser fluorescence scanning, and no significant hybridization is found. The same labeled nucleic acids are then hybridized to an array of 4,000 probes to bacterial signature sequences identified by the methods of this invention. After washing, the pattern of hybridization is observed by confocal laser fluorescence scanning, and interpreted in terms of the known signature sequences for bacteria and the organism is assigned to the genus *Bacillus*.

Example 5

Air Sample

Nucleic acids isolated from an air filtrate are aliquoted into 50 wells of a fluorescence microtiter plate, each well containing a 5'-FITC, 3'-quencher molecular beacon hairpin probe specific for a selected signature sequence. After heating to 95C for 5 minutes, the plate is allowed to cool slowly to room temperature, and fluorescence is read. The pattern of fluorescence is compatible with the presence of a strain of *Staphylococcus*. That is closely related to a known pathogenic strain.

Example 6

Mutated Protease

Nucleic acids of a virus are isolated and amplified from a blood sample and signature sequences are scored using the Qiagen Genomics Masscode sequence detection technology. The presence of particular signature sequences permits identification of a strain bearing a mutation of a previously-known protease, which confers on it resistance to particular therapeutic drugs.

Example 7

Meat Sample

Nucleic acids are isolated from a meat sample claimed to be goose liver and signature sequences are scored using the Third Wave Technologies Invader directed-cleavage assay. The presence of a particular signature sequence indicates the presence of turkey meat as an adulterant.

Example 8

Blood Sample

Blood taken from the bed of a pickup truck owned by a suspected poacher is analyzed for signature sequences of mammalian mitochondrial DNA using individual hybridization assays detected by chemiluminescence produced by an alkaline-phosphatase-conjugated RNA/DNA-specific antibody. The results suggest the blood comes from an animal of the genus *Euarcturos,* and the suspect is arrested on suspicion of poaching the American black bear.

Example 9

Air Sample

Nucleic acids isolated from an air filtrate are aliquoted into 50 wells of a fluorescence microtiter plate, each well containing a 5'-FITC, 3'-quencher molecular beacon hairpin probe specific for a selected 18S rRNA signature sequence. After heating to 95C for 5 minutes, the plate is allowed to cool slowly to room temperature, and fluorescence is read. The pattern of fluorescence is compatible with the presence of both a mold belonging to the genus *Stachybotrys* and a fungus belonging to the genus *Aspergillus*. Two DNA oligonucleotides (one 5' biotinylated) corresponding to two signature sequences found in the sample are used in a PCR reaction to amplify a segment (of predicted length 46 nucleotides, based on the positions of the signature sequences in the 16S rRNA sequence) of rDNA. The biotinylated product is immobilized in single-stranded form and used as a probe for high-affinity, high-specificity detection of a novel species of *Stachybotrys*.

Example 10

Nucleic acids of a virus are isolated and amplified from a blood sample and signature nucleic acid sequences are scored using the Qiagen Genomics Masscode sequence detection technology. Eight signature enzyme activities are also assayed for and two are found, and 24 proteins whose presence can serve as signatures are assayed for by ELISA, and two are detected. The combined presence of particular signature sequences, activities, and proteins permits identification of a particular viral strain.

Example 11

Bioterrorism

Air filtrate from a government building is collected and nucleic acids isolated. rRNA is enriched using DNAse and RNA fragmented by heating. Probes specific to several known bioterrorism agents give negative results. Molecular beacon-based scoring of signature sequences reveals the presence of unexpectedly high concentrations of bacteria with genetic affinity to the genus *Bacillus*. Further investigation reveals an engineered variant strain of *B. anthracis*, and the buildings evacuated. It is noted that the prior art known to Applicants would fail to identify this engineered strain.

MODIFICATIONS

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein. Particularly preferred species and ranges of parameters are partially summarized by Table G.

The nucleic acid sequences included in the database can be any ribosomal RNA, or a fragment thereof, or DNA encoding ribosomal RNA or a fragment thereof, or the DNA spacer region between rRNA genes; or either the genomic DNA or RNA of viruses, or artificial RNAs, or any functional RNA molecule such as RNAse P RNA that is found in a useful variety of organisms. The molecule actually detected may be one that has a sequence related to the molecule represented in the database, for example PCR, NASBA or RT-PCR products, derived from rRNA or rDNA.

Once identified, signature sequences will preferably be used in the design of hybridization probes. In this regard, the set of unique sequences of various lengths are perfect signatures for the specific organism that they are found in and therefore are obvious candidates for use in the design of specific hybridization probes for that organism. If a node is associated with multiple signature sequences, as many are in the case of 16S rRNA, it will be preferable to utilize the one or more with the most favorable hybridization properties. Depending on the experimental setting, the actual probe can preferably incorporate portion or all of either a particular signature sequence or its complement. There are also obvious mathematical relationships between the signature sequences of different lengths. Thus, for example, a 16 base signature sequence that is perfect for node N will necessary show up in the 8 mer signature set as 9 different unique signature sequences for node N (i.e. representing positions 1-8, 2-9,3-10,4-11,5-12,6-13,7-14,8-15,9-16 in the 16-mer). Therefore, one will be able to combine signature sequences in some cases to serve as a starting point in the design of longer probes. Many signature sequences that do not share the type of relationship described above may still be sufficiently near each other in the primary sequence that it will be possible to combine them to design a longer probe. This can be accomplished, for example, by including a—"wildcard" hybridization base such as inosine at certain positions. More generally, a variety of non-standard bases can be used to modify the hybridization properties of a probe based on a signature sequence. Also the properties of a signature sequence can be modified to adapt them for use with organisms represented by another node. Individual monomers in probes or other sequences derived from signature sequences can be modified to facilitate hybridization, or detection. This includes but is not restricted to incorporation of fluorophores, chemically-labile moieties, isotopes, or halogen atoms. Modifications can be incorporated in the course of replication by DNA polymerase or RNA polymerase. Labels can be incorporated in the course of PCR, RT-PCR or NASBA.

Detection can employ a variety of known methods, both those based on sequence-specific hybridization and otherwise. Hybridization can be to RNA or DNA, but also to peptide nucleic acids, locked nucleic acids, branched nucleic acids, cyclic probes, backbone-modified nucleic acids, and base-modified nucleic acids. Array formats (on single or multiple, e.g., bead supports) will often be valuable. Hybridization can lead to the capture of a labeled nucleic acid on a solid support such as a bead, membrane, or array. Labels can be isotopes, chemically-detectable tags, liquid crystals, cleavable chemical tags, fluors, quantum dots, or enzymes such as alkaline phosphatase, ribozymes, or peroxidase. Enzymes can produce heat, color, fluorescence, chemiluminescence, precipitates, bioluminescence, changes in liquid crystalline order, or changes in nucleic acid structure. Hybridization can also lead to production of signals by self-quenching probes such as molecular beacons, or by ribozyme activation, FRET pairs, or changes in plasmon resonance or similar interfacial optical phenomena, in mechanical resonant frequency, in redox activity or electrical conductivity, in electrophoretic or chromatographic mobility, in affinity for chelated metals, minerals, or antibodies or proteins, or in particle or molecular mobility. Robotic methods of preparation and microtiter plates can be employed with the invention to further automate multiple assays.

The method of the invention is especially useful when the hybridization probes consist of every possible sequence of one length. For example, there are 65,536 unique 65,536 octamers. The signature characteristics of every one of these octamers are obtained by the method of the invention for any nucleic acid of interest. When the nucleic acid being used is 16S rRNA or 16S rDNA the same array can be used for any bacterial identification. If multiple organisms are present this will apparent as there will be conflicting signatures. Only the sample preparation procedure would differ. The same array can also be used with any other nucleic acid. Hence by changing the nucleic acid to the positive strand genomic RNA of the flavivirus family, the experimental results would be useful in identifying the closest known genetic relatives of the test virus in this virus group. It is an important aspect of the invention that it is not necessary that all the oligomers in the array need work properly. There is frequently a high redundancy of signature sequences associated with a particular node so that if several fail the node will still give a signal if it is represented in the sample.

Although signature sequences will be preferably be used in conjunction with hybridization methods of various types, it should be noted that these sequences also have unique physical properties. Therefore, if a plurality of signature sequences are generated by experimental means, e.g. by digestion with ribonuclease T1 or a restriction endonuclease, these physical properties can be measured. Mass spectrometry which can comprise matrix-assisted laser desorption ionization (MALDI) or electrospray or TOF or resonance methods can be used to determine mass within 10%, more preferably 2% and most preferably 1% for each sequence. Likewise applications exist where signature sequences can be used in the design of PCR primers to amplify larger regions of DNA or RNA. For example, a completely unknown organism is detected by the method of the invention and best assigned to a large early branching group. The probes that detected this affiliation could then be used as amplification primers to readily obtain a large region for full sequencing or as a longer probe.

Although the invention is preferred for use with functional nucleic acids it can also be used with DNA sequences such as genes that encode protein. In this case, a database of genes for the equivalent protein from a sufficient number and variety of organisms or viruses would be needed. The tree used might be deduced from the genes themselves but in order to avoid possible complications of lateral gene transfer a is preferable to use a tree based on 16S rRNA sequence data.

When the invention is used with viruses, it is necessary to appreciate that all viruses do not share a single common ancestor. There are many distinct groups of viruses, e.g. the Flaviviridae, which is a large family of single stranded positive sense RNA viruses that includes the causative agents of yellow fever, St. Louis encephalitis, Japanese encephalitis, hepatitis C, and Dengue fever. The genomes typically in the size range 9,500-12,500 nucleotides some with DNA genomes and some with RNA genomes. Several common genes exist and hence meaningful phylogenetic trees can be developed which span the entire group. Thus, it is possible to generate signature sequences that are specific for Dengue serotype type II or Dengue in general, etc. The methods of the invention can be used for any virus group as long as a meaningful tree can be produced. However, the sample preparation may require more steps. The different types of nucleic acid involved (single strand positive sense RNA, double stranded DNA etc.) may limit the number of viruses groups that can be detected in one experiment.

Features preferred with the invention in certain cases comprise: the nucleic acid is DNA that encodes ribosomal RNA or a fragment or a complementary sequence of the foregoing; the nucleic acid is RNA complementary to one of the strands of the DNA that is in the spacer region between ribosomal RNA genes or a fragment of the foregoing; the nucleic acid is DNA isolated from the spacer region between ribosomal RNA genes or a fragment of the foregoing; the nucleic acid is any non mRNA produced by the cell or a fragment of the foregoing; the nucleic acid is any mRNA produced by the cell or a fragment of the foregoing; the nucleic acid is genomic DNA or a fragment of the foregoing; the signature quality index $Q_s$ includes terms that weight against false positives and false negatives; the tree contains some multiple branchings but is substantially bifurcating; the genetic affinity of bacteria of eukaryotic organisms is determined; the genetic affinity of more than one bacterial or eukaryotic organism can be determined in a single experiment; wherein the nucleic acid is DNA that encodes ribosomal RNA or a fragment or a complementary sequence of the foregoing; the nucleic acid is RNA complementary to one of the strands of the DNA that is in the sparer region between ribosomal RNA genes or a fragment of the foregoing; the nucleic acid is DNA isolated from the spacer region between ribosomal RNA genes or a fragment of the foregoing; where the nucleic acid is any non mRNA produced by the cell or a fragment of the foregoing.

Other preferred features comprise: the nucleic acid is any mRNA produced by the cell or a fragment of the foregoing;

the nucleic acid is genomic DNA or a fragment of the foregoing; the genetic affinity of more than one virus can be determined in a single experiment; the nucleic acid is a ribosomal RNA or or a fragment or a complementary sequence of the foregoing; the nucleic acid is DNA that encodes ribosomal RNA or a fragment or a complementary sequence of the foregoing the nucleic acid is RNA complementary to one of the strands of the DNA that is in the spacer region between ribosomal RNA genes or a fragment of the foregoing; the nucleic acid is any non mRNA produced by the cell or a fragment of the foregoing the nucleic acid is any mRNA produced by the cell or a fragment of the foregoing; the nucleic acid is genomic DNA or a fragment of the foregoing; the signature probes are of not all of the same length; the signature probes represent signature genes; choosing a tree of relationships that can be reasonably expected to signify genetic relationship was previously published or otherwise generated by a third party, the hybridization probes are complementary or the same sense as the signature sequences; a plurality of signature sequences is combined into one or more larger hybridization probes; a hybridization probe incorporates a portion of the information in a signature sequence; the signature probes are comprised of a nucleic acid analog comprising PNA, 2'-O-methyl DNA or analog thereof; the presence or absence of a signature sequence in a test sample is determined by physical characterization the signature sequences are identified by the method of claim 1. physical characterization is done with mass spectrometry; the nucleic acid molecule is a DNA molecule; the DNA molecule is a cDNA molecule.

The invention may also be applicable in unexpected situations. For example, there are currently a large number of genomes being completely sequenced. When one assembles phylogenetically meaningful clusters of whole genome sequences there are certain genes that are highly characteristic of particular clusters of organisms. These signature genes can be used in the invention to identify unknown organisms, preferably by detecting the presence of activities or gene products associated with the signature genes rather than a nucleic acid assay.

What is claimed is:

1. A method for determining the genetic affinity of organisms or viruses in a test sample containing a target nucleic acid, comprising in combination the steps of:
   A. Obtaining or creating a nucleic acid sequence database of a plurality of sequences, each nucleic acid sequence being from the same corresponding nucleic acid from all organisms or viruses that will be incorporated into the determination;
   B. Obtaining or developing a bifurcating phylogenetic tree having multiple nodes that establishes the genetic affinity between substantially all the organisms or viruses included in the nucleic acid sequence database;
   C. Computationally fragmenting each target nucleic acid sequence such fragmentation being performed in a programmed computer so as to create a signature subsequence database of all nucleic acid subsequences of length N where N is at least seven;
   D. Tabulating in a programmed computer the extent to which the presence of each particular nucleic acid subsequence of length N is characteristic of each node in the bifurcating phylogenetic tree of genetic relationship by examining the occurrence frequency of each subsequence in the target nucleic acid of the organisms and viruses encompassed by or not encompassed by each node in the tree to create a database of characteristic signature sequences herein that extent is identified by: calculating the occurrence frequency and distribution of each subsequence of length N in the sequence database and calculating a signature quality index which measures the extent to which each subsequence of length N is characteristic of each node in the bifurcating node phylogenetic tree of genetic relationships;
   E. Deriving a plurality of signature probes from the signature database of characteristic signature sequences that will be complementary to a portion of the target nucleic acid sequence of the organism or virus if the signature sequence is present;
   F. Hybridizing a plurality of the signature probes representing multiple nodes in the bifurcating tree to the target nucleic acid obtained from the test sample under conditions where a detectable signal will be produced by signature probes that hybridize to the target nucleic acid of the organism or virus and detecting such signals;
   G. Identifying the nodes in the bifurcating phylogenetic tree of genetic relationship that are represented by the signature probes that produced detectable signal, in order to determine the genetic affinity of organisms or viruses in the test sample.

2. A method of claim 1 wherein the signature probes comprise a moiety selected from the group consisting of: RNA, DNA, an analog of RNA or DNA including peptide nucleic acids, 2-O-methyl DNA, branched DNA, and any other nucleic acid molecule that can interact with the test sample nucleic acid by complementarity.

3. A method of claim 1 wherein the hybridization step utilizes a feature selected from the group consisting of an immobilized array of signature probes, molecular beacons and a hybridization step done in solution.

4. A method of claim 1 wherein the detection step utilizes radioactive labels, chemiluminescence and/or fluorescence.

5. A method of claim 1 wherein the bifurcating phylogenetic tree of genetic relationships is generated by parsimony method.

6. A method of claim 1 wherein the most narrowly defined grouping on the tree of relationship comprises a moiety selected from the group consisting of: specific genus, specific species, subgroups; strain, and serotype.

7. A method of claim 1 in which the signature probes are of length 7 or larger and where the nucleic acid is selected from the group consisting of ribosomal RNA, genomic DNA, 10S RNA, RNAse, P RNA, guide RNA, telomerase RNA, snRNAs, scRNAs, and DNA isolated from the spacer region between ribosomal RNA genes and fragments of the foregoing.

8. A method of claim 1 wherein the hybridization step comprises a feature selected from the group consisting of locked nucleic acids, polymerase chain reaction, RTI-PCR, peptide nucleic acids, array detection, and magnetic detection.

9. A method of claim 1 in which the signature probes used have values of Qs averaging less than 0.95 when calculated by the equation:

$$Q_s = (N_{GM}/N_{GT}) \times (1 - (N_M - N_{GM})/NM)$$
$$= (N_{GM}^2)/(N_{GT} \times N_M)$$

in which $N_M$ is the number of probe-matched organisms in the entire tree, $N_{GM}$ is the number of probe-matched organisms in the group of interest and $N_{GT}$ is the number of organisms in the group under consideration.

10. A method of claim 1 wherein the tree comprises 11 or more nodes.

11. A method of claim 1 wherein the target nucleic acid comprises RNA or DNA.

12. A method of claim 1 comprising selecting a target nucleic acid from the group consisting of: ribosomal RNAs, RNAse, P RNA, tmRNA and the DNA that encodes them, spacer region DNA from rRNA gene clusters, mitochondrial DNA, and viral genomic RNAs and DNAs.

13. A method of claim 1 comprising computationally fragmenting each target nucleic acid sequence such fragmentation being performed in a programmed computer so as to create a subsequence database of nucleic acid subsequences of length N that occur in at least two sequences in the nucleic acid database, where N is at least seven; and inspecting the location of positive nodes in the phylogenetic bifurcating tree to determine the genetic affinity of the organism or virus in the test sample.

14. A method of claim 1 where the same target nucleic acid sequence is obtained from viruses.

15. A method of claim 1 in which the nucleic acid database is comprised of at least 12 sequences of a target RNA or DNA, the sequences being derived from different organisms or viruses and being at least 30% identical over at least one subsequence of at least 50 nucleotides.

16. A method of claim 1 wherein all subsequences of length 7 or longer that occur in less than two sequences in the nucleic acid database are not considered when creating a database of characteristic signature sequences.

17. A method for determining the genetic affinity of organisms or viruses in a test sample containing a nucleic acid, comprising in combination the steps of:
A. Obtaining or creating a nucleic acid sequence database of a plurality of sequences, each nucleic acid sequence being from the same corresponding nucleic acid, from all organisms or viruses that will be incorporated into the determination;
B. Obtaining or developing a bifurcating phylogenetic tree having multiple nodes that establishes the genetic affinity between-the organisms or viruses included in the nucleic acid sequence database;
C. Calculating the occurrence frequency and distribution of each subsequence of length N that occur in at least two sequences in the nucleic acid database, in the subsequence database;
D. Tabulating in a programmed computer a signature quality index which measures the extent to which each subsequence of length N is characteristic of each node in the bifurcating node phylogenetic tree of genetic relationships by computationally fragmenting each target nucleic acid sequence such fragmentation being performed in a programmed computer so as to create a subsequence database of nucleic acid subsequences of length N that occur in at least two sequences in the nucleic acid database, where N is at least seven;
E. Deriving a plurality of signature probes from the signature database of characteristic signature sequences that will be complementary to a portion of the target nucleic acid sequence of the organism or virus if the signature sequence is present;
F. Hybridizing the signature probes to the target nucleic acid obtained from the test sample under conditions where a detectable signal will be produced by signature probes that hybridize to the target nucleic acid of the organism or virus and detecting such signals;
G. Identifying the nodes in the bifurcating phylogenetic tree of genetic relationship that are represented by the signature probes that produced detectable signal, in order to determine the genetic affinity of the organism or virus in the test sample.

18. A method of claim 17 in which the signature quality index, Qs, is calculated by substantially the equation:

$$Q_s = (N_{GM}/N_{GT}) \times (1 - (N_M - N_{GM})/NM)$$
$$= (N_{GM}^2)/(N_{GT} \times N_M)$$

in which $N_M$ is the number of probe-matched organisms in the entire tree, $N_{GM}$ is the number of probe-matched organisms in the group of interest, and $N_{GT}$ is the number of organisms in the group under consideration.

19. A method of claim 1 in which the oligonucleotides or sequences of length N comprise genes.

20. A method of claim 17 in which a measure of signature quality is calculated by considering the frequency of occurrence of each subsequence of length N in a particular group of organisms or viruses as well as its presence in other organisms not belonging to that group of organisms or viruses.

21. A method according to claim 17 wherein the tree comprises eleven or more nodes, N equals 7 or more and the nucleic acid database comprises 12 or more sequences and wherein the detection step comprises analysis by mass spectrometer.

* * * * *